(12) United States Patent
Krueger et al.

(10) Patent No.: US 8,618,477 B2
(45) Date of Patent: *Dec. 31, 2013

(54) METHOD AND APPARATUS FOR CHEMICAL AND BIOLOGICAL SAMPLE SEPARATION

(75) Inventors: Clinton Alawn Krueger, Milton, MA (US); Ching Wu, Acton, MA (US)

(73) Assignee: Excellims Corporation, Acton, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/584,388

(22) Filed: Aug. 13, 2012

(65) Prior Publication Data

US 2012/0305761 A1 Dec. 6, 2012

Related U.S. Application Data

(63) Continuation of application No. 12/695,111, filed on Jan. 27, 2010, now Pat. No. 8,242,442, which is a continuation of application No. 12/471,101, filed on May 22, 2009, now Pat. No. 8,106,352, which is a continuation of application No. 11/618,430, filed on Dec. 29, 2006, now Pat. No. 7,576,321, said application No. 12/695,111 is a continuation-in-part of application No. 12/610,306, filed on Oct. 31, 2009, now Pat. No. 8,063,361, which is a continuation-in-part of application No. 12/026,192, filed on Feb. 5, 2008, now Pat. No. 7,696,474, and a continuation-in-part of application No. 12/577,062, filed on Oct. 9, 2009, now Pat. No. 8,217,338.

(60) Provisional application No. 61/147,646, filed on Jan. 27, 2009.

(51) Int. Cl.
*H01J 49/26* (2006.01)
*B01D 59/44* (2006.01)

(52) U.S. Cl.
USPC ............ 250/288; 250/281; 250/282; 250/287

(58) Field of Classification Search
USPC ................................. 250/288, 281, 282, 287
See application file for complete search history.

(56) References Cited

U.S. PATENT DOCUMENTS

| 7,576,321 | B2* | 8/2009 | Wu ............................... 250/286 |
| 8,106,352 | B2* | 1/2012 | Ching ........................... 250/288 |
| 8,217,338 | B2* | 7/2012 | Krueger et al. ............... 250/282 |
| 8,242,442 | B2* | 8/2012 | Krueger et al. ............... 250/288 |

* cited by examiner

*Primary Examiner* — Nikita Wells

(57) ABSTRACT

The present invention involves a series of shifting reagents that selectively interact with a targeted functional group of biological molecules, pharmaceutical drugs, small molecules, chemicals, chemical agents, or explosives resulting in a structure selective based drift time shift in the IMS. Additional energy is used to enhance the mobility based separation; in particular, the energy level can be tuned.

17 Claims, 14 Drawing Sheets

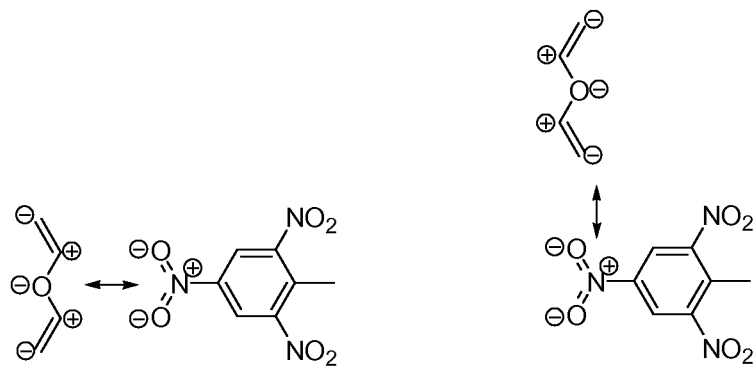
Figure 9A  Figure 9B
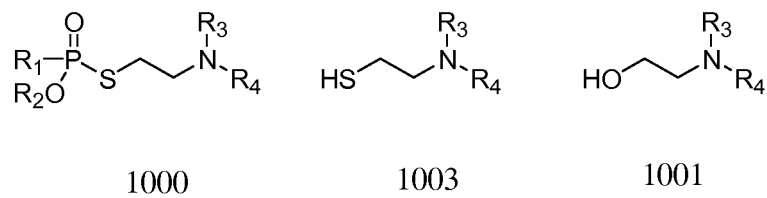
1000  1003  1001
Figure 10
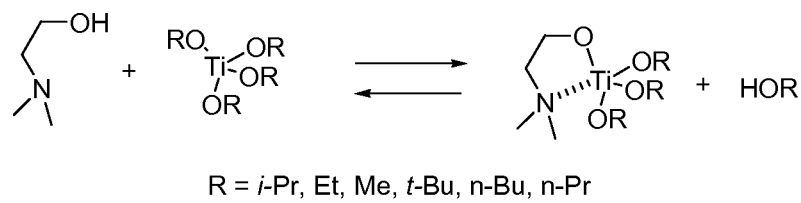
R = *i*-Pr, Et, Me, *t*-Bu, n-Bu, n-Pr
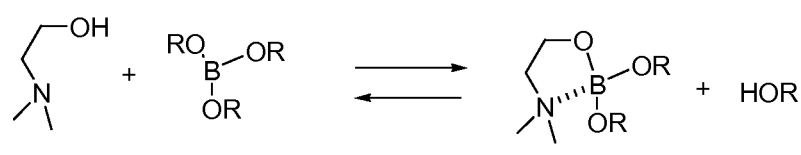
R = *i*-Pr, Et, Me, *t*-Bu, n-Bu, n-Pr
Figure 11

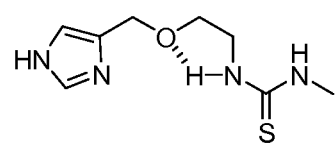
Figure 13
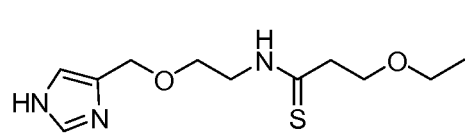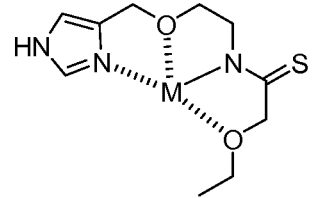
Figure 14A          Figure 14B

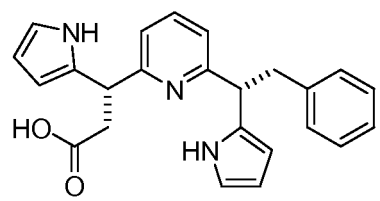 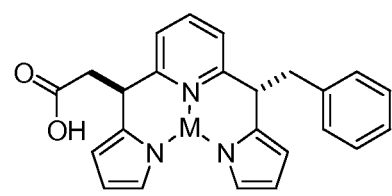
Figure 15A  Figure 15B
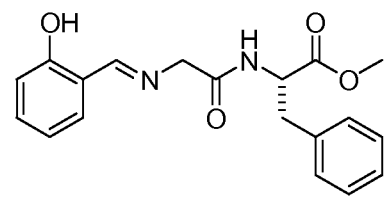
Figure 16

1801

1803

1805

METHOD AND APPARATUS FOR CHEMICAL AND BIOLOGICAL SAMPLE SEPARATION

CROSS-REFERENCE TO RELATED APPLICATIONS

The present application is a continuation of U.S. patent application Ser. No. 12/695,111, filed on Jan. 27, 2010, now U.S. Pat. No. 8,242,442, which is a continuation in part of U.S. patent application Ser. No. 12/471,101, filed on May 22, 2009, now U.S. Pat. No. 8,106,352, which is a continuation of U.S. patent application Ser. No. 11/618,430, filed on Dec. 29, 2006, now U.S. Pat. No. 7,576,321, and is a continuation in part of U.S. patent application Ser. No. 12/610,306, filed on Oct. 31, 2009, now U.S. Pat. No. 8,063,361, which is a continuation in part of U.S. patent application Ser. No. 12/026,192, filed on Feb. 5, 2008, now U.S. Pat. No. 7,696,474, and is a continuation in part of U.S. patent application Ser. No. 12/026,192, filed on Feb. 5, 2008, now U.S. Pat. No. 7,696,474, and is a continuation in part of U.S. patent application Ser. No. 12/577,062, filed Oct. 9, 2009, now U.S. Pat. No. 8,217,338, and claims the benefit of and priority to corresponding U.S. Provisional Patent Application No. 61/147,646, filed Jan. 27, 2009 respectively, the entire content of the application is herein incorporated by reference. The contents of all of these patent applications are incorporated herein by reference.

BACKGROUND OF THE INVENTION

Ion mobility spectrometers (IMS) have become a common tool for detecting trace amounts of chemical and/or biological molecules. Compared to other spectrometric chemical analysis technologies, e.g., mass spectrometry, IMS is a relatively low resolution technique. The IMS advantages of very high sensitivity, small size, low power consumption, and ambient pressure operation are in some cases completely offset, or at a minimum, reduced by the lack of sufficient resolution to prevent unwanted responses to interfering chemical and/or biological molecules. The false positives that result can range from minor nuisances in some scenarios to major headaches in others. Interfering chemical and/or biological molecules can have very similar ion mobilities which in turn can significantly limit detecting and identifying low levels of the targeted chemical and/or biological molecules in the sample.

Another IMS resolution issue can occur as the molecules increase in molecular complexity (size, number of stereogenic centers, number of chiral centers, number of functional groups, etc). More conformations are possible due to the flexibility of the molecule, which can thus adopt multiple different conformations while traveling down the drift tube.

The present state of the art ion mobility spectrometers lack the ability to: directly reduce the occurrence of interfering chemical and/or biological molecules in a sample's analysis, limit the number of possible conformations of a molecule, and report the relative difference of a molecule to an internal standard. The molecular geometry of molecules can be utilized in the efforts to explore new analytical spectroscopic/spectrometric techniques. It is the purpose of this invention to overcome these obstacles by making the use of a molecule's molecular geometry. A chemical modifier and/or a shifting reagent can be used to reduce the occurrence of interfering chemical and/or biological molecules in a sample's analysis. Differentiating components in a sample in an IMS can be done by utilizing at least one additional property of the components besides their ion mobility and/or ion mobility differences. Adding energy to the components of the sample to be separated can enhance separation in IMS.

SUMMARY OF THE INVENTION

The present invention involves a series of shifting reagents that selectively interact with a targeted functional group of biological molecules, pharmaceutical drugs, small molecules, chemicals, chemical agents, or explosives resulting in a structure selective based drift time shift in the IMS. The invention allows detecting and confirming samples using one or more ion mobility based spectrometers. Certain embodiments of the present invention involve a series of shifting reagents that selectively interact with a targeted functional group of biological molecules, pharmaceutical drugs, small molecules, chemicals, chemical agents, or explosives resulting in a structure selective based drift time shift in the IMS. In one aspect of the present invention, at least one chemical modifier and/or shifting reagent are added to the IMS that interacts selectively with at least one component of the sample. The component may be impurities and/or interferences in the sample whereby the chemical modifier and/or shifting reagent enhance sample resolution by shifting the components drift times and/or other ion mobility characteristics. The present invention describes differentiating components in a sample in an IMS using at least one additional property of the components besides their ion mobility and/or ion mobility differences. The present invention also describes method and apparatus to add energy to the components of the sample to be separated, shifting reagents and/or chemical modifiers to enhance separation in IMS.

BRIEF DESCRIPTION OF THE DRAWINGS

The foregoing and other aspects, embodiments, and features of the inventions can be more fully understood from the following description in conjunction with the accompanying drawings. In the drawings like reference characters generally refer to like features and structural elements throughout the various figures. The drawings are not necessarily to scale, emphasis instead being placed upon illustrating the principles of the inventions.

FIG. 1 shows the molecular geometry of a molecule may be due to the molecules' ring topology, from one or more of the functional groups found in the molecule, or may be part of the entire molecule.

FIG. 2 shows the ion mobility spectrum of chemicals introduced into an ion mobility based spectrometer.

FIG. 3 shows the mechanism for the epoxidation of cyclohexene with hydrogen peroxide using phenol as a catalyst.

FIG. 4 shows the chemoselective interaction of the peroxide functional group in TATP with cyclopentanediol through hydrogen bonding.

FIG. 5 shows hydrogen bonding with empty orbitals of boron and titanium.

FIG. 6 shows a dipole-dipole interaction with TATP and dimethyl malonate.

FIG. 7 shows multiple interaction points between boric acid and nitro compounds.

FIG. 8 shows a dipole-dipole interaction of 2,5-Dimethylfuran and TNT.

FIGS. 9A-B shows two possible manners in which divinyl ether interacts with TNT.

FIG. 10 shows two possible degradation products of the VX/V-type nerve agent.

FIG. 11 shows the reversible interactions of $Ti(OR)_4$ and $B(OR)_3$ with bidentate ligands.

FIG. 12 shows hydrogen bonding interactions between chemical modifiers and degradation product.

FIG. 13 shows an intramolecular hydrogen bonding that produces a conformationally restricted molecule.

FIGS. 14A-B shows a unrestricted molecule FIG. 14A and a metal bound complex 14B.

FIGS. 15A-B shows a unrestricted molecule with 2 chiral centers 15A and a metal bound complex 15B.

FIG. 16 shows a molecule with one chiral center.

FIGS. 17A-C shows different interactions with the molecule.

Figure 1:
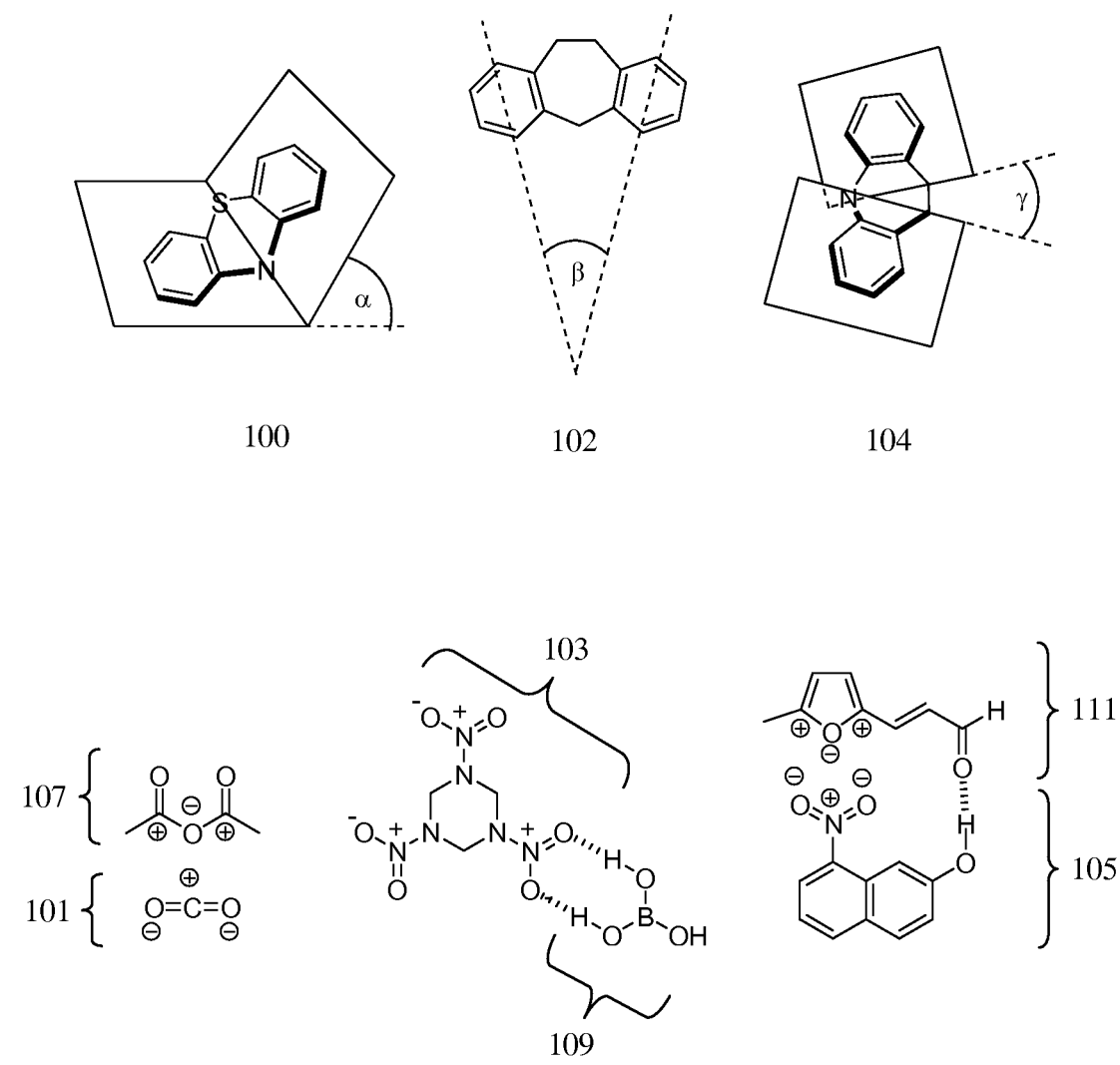

FIG. 25A-D shows: (25A) shows TNT 2501 and MATB 2503 being converted to quinoid ions using tetraethylammonium hydroxide and n-butanol in the presence of other components 2505 of the sample, (25B) shows a spectrum displaying the drift times of the sample without using a shifting reagent, (25C) depicts the nitro based explosives 2501 and 2503 that are part of the sample being shifted to longer drift times due to shifting reagent converting them to 2502 and 2504, which have a longer drift time, and (25D) shows a spectrum displaying the drift times of the sample using a shifting reagent. Compounds 2502 and 2504 are at higher drift times where they are clear of interferences, such as the other components 2505.

DETAILED DESCRIPTION OF VARIOUS EMBODIMENTS

Unless otherwise specified in this document the term "ion mobility based spectrometer" is intended to mean any device that separates ions based on their ion mobilities and/or mobility differences under the same or different physical and/or chemical conditions, the spectrometer may also include detecting the ions after the separation process. Many embodiments herein use the time of flight type IMS as examples; the term ion mobility based spectrometer shall also include many other kinds of spectrometers, such as differential mobility spectrometer (DMS) and field asymmetric ion mobility spectrometer (FAIMS). Unless otherwise specified, the term ion mobility spectrometer or IMS is used interchangeable with the term ion mobility based spectrometer defined above.

As used herein, the term "analytical instrument" generally refers to ion mobility based spectrometer, MS, and any other instruments that have the same or similar functions. Unless otherwise specified in this document the term "mass spectrometer" or MS is intended to mean any device or instrument that measures the mass to charge ratio of a chemical/biological compounds that have been converted to an ion or stores ions with the intention to determine the mass to charge ratio at a later time. Examples of MS include, but are not limited to: an ion trap mass spectrometer (ITMS), a time of flight mass spectrometer (TOFMS), and MS with one or more quadrupole mass filters The phrase "and/or," as used herein in the specification and in the claims, should be understood to mean "either or both" of the elements so conjoined, i.e., elements that are conjunctively present in some cases and disjunctively present in other cases.

Unless otherwise specified in this document the term "chemical and/or biological molecule" is intended to mean single or plurality of particles that are, either charged or not charge, derived from atoms, molecules, particles, and subatomic particles.

In one aspect of the present invention, at least one chemical modifier is added to the drift gas that interacts selectively with a targeted molecular geometry in at least one component of the sample, in particular, in a drift tube. The component of the sample can be: a chemical and/or biological molecule that is of interest or the component may be impurities and/or interferences in the sample whereby the chemical modifier enhances sample resolution by shifting the components drift times. By utilizing the components' molecular geometry, the chemical modifier interacts preferentially with one component over another through an ion-molecular interaction. The chemical modifier interaction forces, may include; hydrogen bonds, van der Waals forces, dipole-dipole, steric hindering effects, coordinate covalent bond, metallic bond, ionic bond, non-covalent bond, weak covalent nature, antibonding, chemical affinity, intermolecular bonding, intramolecular bonding, cation-pi interaction, mechanical bond, halogen bond, aurophilicity, intercalation, stacking, entropic force, chemical polarity, low-barrier hydrogen bond, symmetric hydrogen bond, or combinations of these, but is not limited to only these.

In another aspect of the present invention, the chemical modifier can be added to the sample prior to ionization and/or directly introducing them into the reaction region of the drift tube of time of flight type of IMS. In case of other type of ion mobility based spectrometer, the modifier could be added into the carrier gas before or during separation.

Molecular geometry or molecular structure is the three dimensional arrangement of the atoms that constitute a molecule. The molecular geometry of a molecule can be used to help make predictions about crystal structure, dipole moment, reactivity, bond lengths, bond angles, to name a few. There are six basic geometrical shapes for small molecules and/or individual functional groups: linear, trigonal planar, tetrahedral, octahedral, pyramidal, and bent. Larger molecules often have a unique topology that is established by one or more functional groups and/or the core shape of the molecule that gives rise to their molecular geometry. This unique topology can arise from the fact that each atom within a molecule occupies a certain amount of space, i.e. steric effect and elicit a specific steric attraction. Steric attraction occurs when molecules have geometries that are optimized for interaction with one another. In these cases molecules will react/interact with each other most often in specific arrangements. A non-limiting example of a larger molecule with a specific topology arises from the core shape of the molecule is shown in FIG. 1. The $\alpha$ angle of molecule 100, the $\beta$ angle of molecule 102, and the $\gamma$ angle of molecule 104 gives rise to a ring topology that is unique. As shown in FIG. 1, the molecule's geometrical shape may be part of the entire molecule, such as carbon dioxide 101 (linear geometry), or may be from one or more of the functional groups found in the molecule, such as the nitro functional group found in cyclotrimethylenetrinitramine (RDX) 103 (trigonal planar geometry). In addition, different functional group combinations within a molecule can set up a molecules' molecular geometry, such as 1-nitro-7-naphthol 105. Each functional group's atoms and hybridization establishes the molecules' unique molecular shape. The molecular geometry of each functional group can be used to elicit specific ion-molecular interactions with a chemical modifier. The chemical modifier's molecular geometry would need to be complementary to the component to be separated/resolved molecular geometry. For example, since carbon dioxide (component to be separated/resolved) 101 has a linear geometry, a chemical modifier that also displays a linear geometry would be necessary for a dipole-dipole ion-molecular interaction to take place. Although the point charges are not exactly in a linear geometry for acetic anhydride (chemical modifier) 107, the molecular geometry may be good enough to induce a force between the two molecules 101 and 107. If the targeted molecular geometry of RDX 103 is one of the three nitro functional groups, then a chemical modifier would need to meet these geometrical requirements by having a complementary molecular geomentry. The nitro group has a trigonal planar geometry, therefore boric acid 109 would be a good choice for a chemical modifier because of boric acid's trigonal planar geometry. The ion-molecular interaction between these two molecules 103 and 109, is through hydrogen bonding. Different functional group combinations within a molecule set up a molecules' geometric frame, such as 1-nitro-7-naphthol 105. A nitro group along with an alcohol functional group in the same molecule with an aromatic napthyl ring core sets an overall planar molecular geometry. A chemical modifier with a planar geometric frame, such as molecule 111 may be advantageous to exploit a dipole-dipole interaction with the nitro group functionality along with a hydrogen bonding interaction with the alcohol functional group.

Functional groups are specific groups of atoms within molecules that are responsible for the characteristic interaction of these molecules in chemical reactions (forming and breaking of chemical bonds) and attraction forces. The molecular shape of the molecules are dictated by the combinations and locations of the functional groups that make up a molecule's geometric frame and therefore influence the molecules interactions between molecules. These interactions or attraction forces may include; hydrogen bonds, van der Waals forces, dipole-dipole, steric hindering effects, coordinate covalent bond, metallic bond, ionic bond, non-covalent bond, covalent bond, weak covalent nature, antibonding, but is not limited to only these.

As used herein, the term "functional group" may include the following specific groups of atoms within molecules; acetal, acetoxy group, acetyl, acid anhydride, acryl group, acyl, acyl halide, acylal, acyloin, acysilane, alcohol, aldehyde, aldimine, alkane, alkene, alkoxide, alkoxy group, alkyl, alkyl cycloalkane, alkyl halide, alkyl nitriles, alkyne, allene, allyl, amine, amide, amidine, amine oxide, amino, ammonium, amyl, aryl, azide, aziridine, azo compound, azoxy, benzoyl, benzyl, beta-lactam, bisthiosemicarbazone, biuret, boronic acid, butyl, carbamate, carbine, carbinol, carbocyclyl, carbocyclylic, carbocycle, carbocyclo, carbodiimide, carbonate ester, carbonyl, carboxamide, carboxyl group, carboylic acid, chloroformate, crotyl, cumulene, cyanamide, cyanate, cyanate ester, cyanimide, cyanohydrin, cycloalkane, cycloalkene, cycloalkyne, cyclopropane, diazo, diazonium compound, diol, disulfide, enamine, enol, enol ether, enolate anion, enone, enyne, episulfide, epoxide, ester, ether, ethyl group, glycosidic bond, guanidine, halide, halohydrin, halogen, haloketone, hemiacetal, hemiaminal, heterocyclic group, heterocyclic, heterocycle, heterocyclyl, heterocyclo, heteroaryl, hydrazide, hydrazine, hydrazone, hydroperoxide, hydroxamic acid, hydroxyl, hydroxyl radical, hydroxylamine, hydroxymethyl, imine, iminium, isobutyramide, isocyanate, isocyanide, isopropyl, isothiocyanate, ketal, ketene, ketenimine, ketone, ketyl, lactam, lactol, mesylate, metal acetylide, methane, methoxy, methyl group, methylene, methylenedioxy, N-oxoammonium salt, nitrate, nitrile, nitrilimine, nitrite, nitro compound, nitroamine, nitronate, nitrone, nitronium ion, nitrosamine, nitroso, nitrosyl, nonaflate, organic peroxide, organosulfate, organosulfur compound, organophosphorous, organohalide, orthoester, osazone, oxime, oxon, pentyl, peptide, peroxide, persistent carbine, phenyl group, phenylene, phosphalkyne, phosphate, phosphinate, phosphine, phosphine oxide, phosphinite, phosphite, phosphonate, phosphonite, phosphonium, phosphorane, propargyl, propyl, propynyl, radical, Schiff base, selenol, selenocarboxylic acid, selenoether, selenonic acid, semicarbazide, semicarbazone, silyl enol ether, silyl ether, sulfide, sulfinic acid, sulfenic acid, sulfonamide, sulfonate, sulfonic acid, sulfonyl, sulfoxide, sulfuryl, tellurols, thial, thioacetal, thioaldehyde, thioamide, thiocarboxy, thiocaroxylic acid, thiocyanate, thioester, thioether, thioketal, thioketone, thiol, thiourea, tosyl, triazene, triflate, trifluoromethyl, trihalide, trimethylsilyl, triol, urea, vanillyl, vinyl, vinyl halide, xanthate, ylide, ynolate but is not limited to only these.

Unless otherwise specified in this document the term "chemical modifier" is intended to mean single or plurality of chemicals and/or biological(s) which to certain degrees selectively interacts with at least one targeted molecular geometry in at least one component of the sample. In addition, the chemical modifier may have one or more chiral center(s).

Unless otherwise specified in this document the term "targeted molecular geometry" is intended to mean the three dimensional arrangement of the atoms that constitute a molecule. The targeted molecular geometry can be: the entire molecule, one or more functional groups in the molecule, the geometric frame whereby different functional group combinations within a molecule set up a molecule's molecular geometry, the topology of the molecule, the steric effects in the molecule, but not limited to only these.

Unless otherwise specified in this document the term "complementary molecular geometry" is intended to mean the molecular geometry of the chemical modifier is similar to the targeted molecular geometry to a degree in which the interaction between the component of the sample to be separated/resolved and the chemical modifier is selective to some extent over non-targeted molecular geometries. The complementary molecular geometry can be: the entire molecule, one or more functional groups in the molecule, the geometric frame whereby different functional group combinations within a molecule set up a molecule's molecular geometry, the topology of the molecule, the steric effects in the molecule, linear, trigonal planar, tetrahedral, octahedral, pyramidal, bent, but not limited to only these.

In the present invention, one or more chemical modifiers are generally infused into the drift gas stream and introduced into the ion mobility based spectrometer. During the collisions/encounter between one or more components of the sample and one or more chemical modifiers, interactions are transient in nature. The chemical modifier does not involve a derivatization of the component of the sample via a permanent covalent bond, such as that used in covalent synthesis. The chemical modifier does not involve ion-molecule reactions such as the $S_N2$ nucleophilic displacement reactions of chloride anions with alkyl bromides in a nitrogen buffer gas. Instead, the chemical modifier involves ion-molecule interactions in the form of transient complexes such as hydrogen bonds, van der Waals forces, dipole-dipole, steric hindering effects, but not limited to only these. As the transient complexes formation and deformation process rapidly repeats in the ion mobility based spectrometer, a structure selective resolution of components of the sample can be observed. The contribution of the chemical modifier to the average measured mobility shift should be concentration dependent and analytically quantifiable. The degree of interaction between the components of the sample and the chemical modifiers can also be altered by altering the type and concentration of the chemical modifiers and gas temperature, pressure and flow rate in the drift tube. Multiple point interactions between sample and chemical modifier could potential result in more substantial mobility shift.

Figure 2:
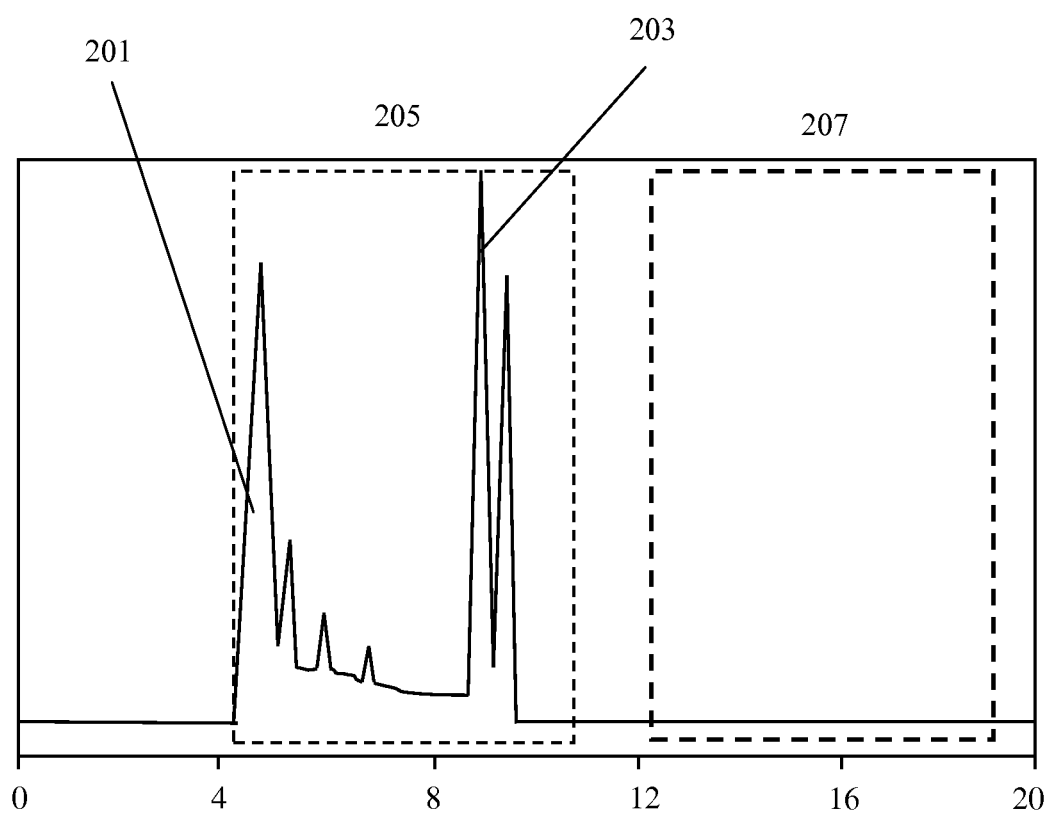

Certain embodiments of the present invention involve a series of chemical modifiers that selectively interact with the targeted molecular geometry of chemical agents or explosives resulting in a structure selective based drift time shift in the IMS. A drift gas chemical modifier can selectively increase nitro based compounds drift time according to the selected modifier's molecular geometry. In the following non-limiting example, the chemical modifier's targeted molecular geometry is to a nitro functional group. The drift time of nitro based explosives such as TNT, RDX, and Nitroglycerine all are moved away from their original drift time eliminating common interference problems in IMS through the use of designed gas phase ion chemistry. FIG. 2 shows an ion mobility spectrum resulting from a laboratory test in which a known amount of TNT was introduced to the system. During the course of detection, multiple peaks were detected and only one of them is directly related to the component TNT 203. Another predominant peak 201 is the instrument background ion. Note that there is significantly less or no interference existing in the relatively long drift time region 207. In this particular example, the several other interferant peaks distributed between these two peaks; most of them are in the low drift time range. In addition, this spectrum was acquired in a laboratory environment whereby field samples commonly show more complex ion mobility spectra. Unfortunately, most nitro based targeted analytes have very similar ion mobilities as the interferants. The nitro based explosives have a drift time in the region as shown within the 205 dashed line box in FIG. 2. In this region, detection windows and thresholds are a compromise between sensitivity and false alarm rate and significantly limit detecting low levels of explosives and make it impossible to detect explosives. A structure selective ion-molecular interaction (SSIMI) can be used to selectively adjust the drift time of components in a sample of interest, to a desired region of the IMS spectrum where few or no interfering chemicals exist. As FIG. 2 illustrates, if the drift time of all nitro based explosives is shifted the long drift time range 207 dashed line box, there is very low probability for interference; the detection threshold could be reduced to a much lower level.

The following examples are non-limiting. The targeted molecular geometry could be used for similar ion-molecular interactions.

Figure 3:
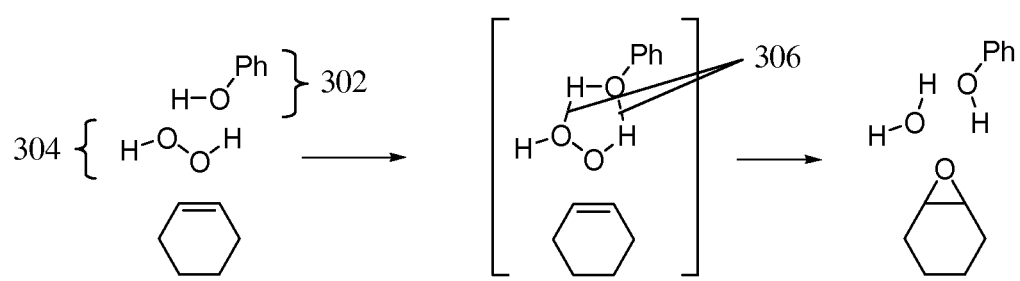
Figure 4:
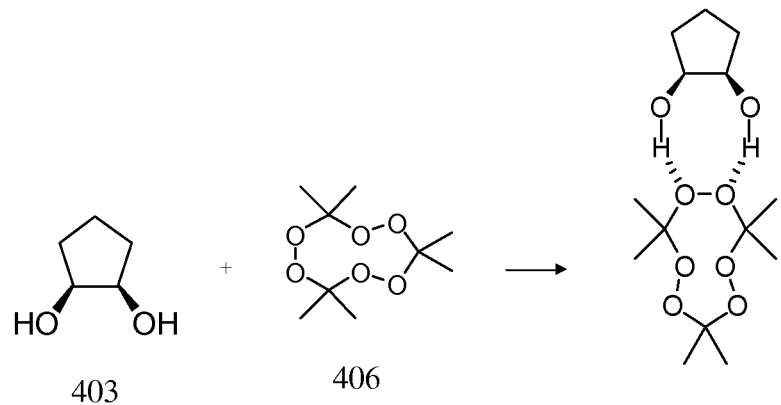
Figure 5:
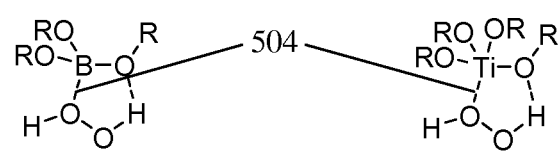
Figure 6:
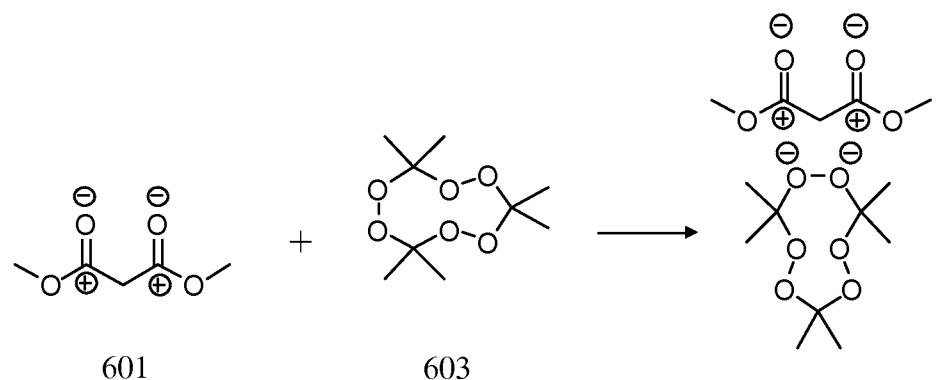

Detecting peroxides and their precursors is very difficult for the existing ion mobility spectrometers. Current IMS based systems can detect the break down products of triacetonetriperoxide (TATP) but exhibit high false alarm rates in a short drift time detection window, and they are not able to detect hydrogen peroxide. To resolve the peroxide detection issue, several gas phase interaction mechanisms can be used to realize SSIMI. A hydrogen bonding interaction between chemical modifier and the targeted molecular geometry of a peroxide functionality in TATP is the next non-limiting example. In organic synthesis, epoxidation of alkenes using hydrogen peroxide is typically accomplished by employing a metal catalyst. Recently, it has been shown that organic, non-metal compounds are capable of activating $H_2O_2$ for the epoxidation of olefins. As shown in FIG. 3, Jacobs uses phenol 302 as the catalyst to activate hydrogen peroxide 304 through hydrogen bonding 306. The two reacting molecules must attain a specific geometry to permit hydrogen bonding to occur. This reaction demonstrates a strong interaction between phenol and hydrogen peroxide for epoxidation of cyclohexene to occur. By using this geometrically aligned hydrogen bonding interaction, the drift time of a hydrogen peroxide sample using phenol as a modified drift gas will shift the hydrogen peroxide sample to a longer drift time due to this hydrogen bonding interaction. Levels of chemical modifiers in the ppm range can cause drift times to shift by milliseconds. The amount of shift depends upon the strength of ion-molecular interaction forces, the degree of molecular complementary molecular geometry with the peroxide, modifier concentration, and operating parameters (such as temperature). Similarly, other chemical modifiers, such as perfluorinated alcohol solvents could also be used to achieve the effect of a structure selective interaction with peroxides. In addition, cis-1,2-cyclopentanediol 403 could be used to selectively interact with triacetone triperoxide (TATP) 406 using multiple point hydrogen bonding to shift the drift time of TATP to a range with less interference from other components in the sample as shown in FIG. 4. TATP has three peroxide functional groups taken together to form a ring. The molecular geometry of the peroxide functionality contained in the ring positions the lone pairs on each oxygen in a orientation such that two hydrogen bond donors would need to be in the same plane, such as that found in cis-1,2-cyclopentanediol 403. In addition to hydrogen bonding, elements with empty orbitals 504 and substituents that are hydrogen bond acceptors could be used to interact with electron rich peroxides such as those that are shown in FIG. 5. Some non-limiting examples are: oxophilic boron and titanium based modifiers such as $Ti(OEt)_4$, $Ti(i-OPr)_4$, $B(OMe)_3$, $B(OEt)_3$ and $B(i-OPr)_3$, etc. can be used for their ability to interact with peroxide functionality in a variety of drift tube conditions. This group of modifiers has boiling points from 58 to 232° C. and are suitable to be introduced as a low concentration (ppm) vapor mixture in the drift gas. Another gas phase structure selective ion-molecular interaction that could be used is a dipole-dipole interaction. FIG. 6 shows the interaction between dimethyl malonate 601 and TATP 603. This non-limiting example demonstrates a two-point dipole-dipole interaction with a great degree of selectivity from being geometrically aligned. Dimethyl malonate is specifically chosen to match the molecular geometry and interact with the O—O functionality in TATP.

Figure 7:
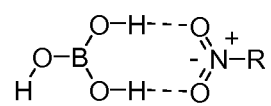
Figure 7:
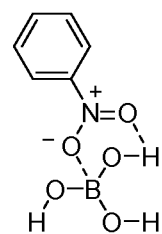

With a similar ion-molecular interaction illustrated for peroxides, the drift time of nitro based explosives could also be shifted. Some non-limiting examples are discussed for ion-molecular interaction forces, such as hydrogen bonding and a dipole-dipole interaction. FIG. 7 illustrates two possible hydrogen bonding schemes that demonstrate multiple interaction points between boric acid and nitro compounds. Nitro compounds contain one or more nitro functional groups. The nitro functional groups are "planar" structures, therefore boric acid is chosen because it's trigonal planar geometry which is complementary to the targeted molecular geometry.

Figure 8:
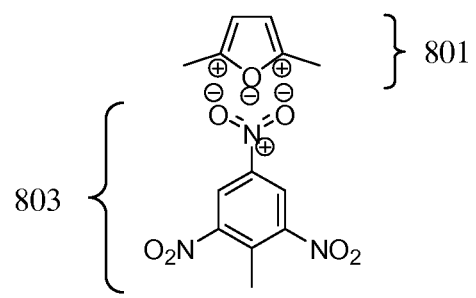

FIG. 8 shows a dipole-dipole interaction of 2,5-Dimethylfuran 801 and an aromatic nitro compound 803 (e.g. TNT). In this interaction, the geometry of the modifier is critical for a successful drift time shift because the dipole-dipole interaction normally is a near range interaction. Divinyl ether 902 interacts with TNT 904 either in a side-to-side manner FIG. 9A or top-to-bottom manner FIG. 9B. The discussed examples are non-limiting, other molecules that have similar structural functionality and charge distribution can also be used as modifiers to shift drift time of nitro compounds.

Figure 12:
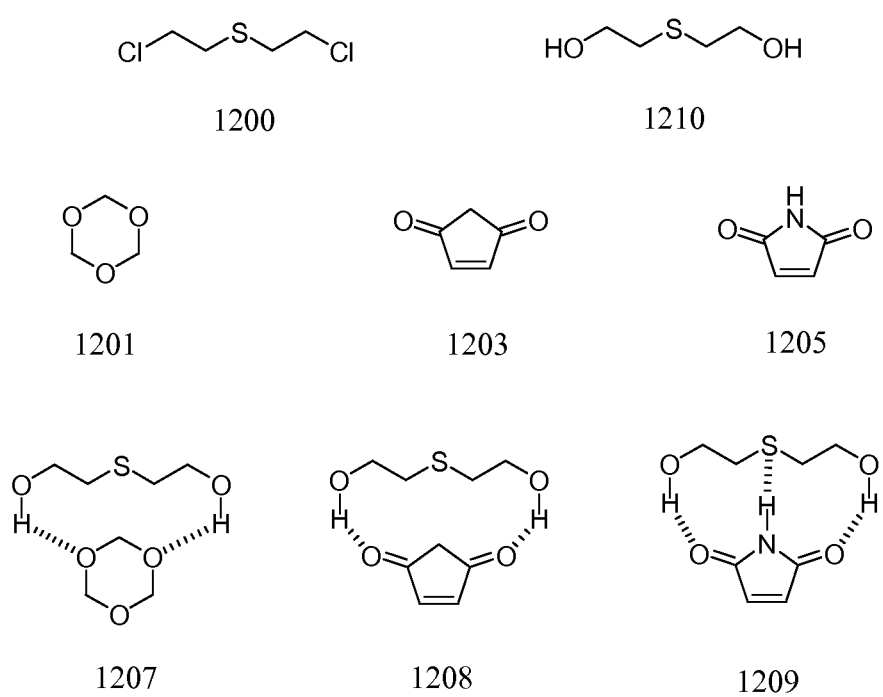

Many other molecules can be used for the SSIMI method, such as, but not limited to the degradation products of nerve agents. FIG. 10 shows two possible degradation products of the VX/V-type nerve agent 1000, an amino alcohol 1001 and an amino thiol 1003, that can selectively interact with lewis acids since they are bidentate ligands. In addition, oxygen and sulfur have strong potential to interact with boron and titanium in a reversible fashion. As shown in FIG. 11, $Ti(OR)_4$ and $B(OR)_3$ can have strong reversible interactions with various molecules. The degradation products of sulfur mustard 1200 could selectively form hydrogen bonding with several modifiers, depending on the modifier's geometrical positioned functionality and strength of interaction. FIG. 12 shows the modifier structures, 1,3,5-Trioxane 1201, 4-Cyclopentene-1,3-dione 1203, and Maleimide 1205, and the possible interactions 1207, 1208, & 1209 with degradation and product 1210 of the sulfur mustard 1200.

The SSIMI resolution/separation method can be used to identify biological molecules as well as chemicals. Trypsin is used to break down proteins. Hence it has been used widely in various biotechnological processes. Trypsin predominantly cleaves peptide chains at the carboxyl side of the amino acids lysine (Lys) and arginine (Arg), except when either is followed by proline. Trypsin is commonly used in biological research during proteomics experiments to digest proteins into peptides for mass spectrometry analysis, e.g. in-gel digestion. Trypsin is particularly suited for this, since it has a very well defined specificity, as it hydrolyzes only the peptide bonds in which the carbonyl group is contributed either by an Arg or Lys residue. The Arg or Lys functionality exposed in these peptides along with the carboxylic acid functionality at one end of the peptide produces a defined molecular geometry that a chemical modifier can be designed to selectively interact with. Since the Arg functionality is different than the Lys functionality and they both have different molecular geometries, then a chemical modifier can selectively interact with one over the other. For example, after a Trypsin digest, the researcher can add a chemical modifier to the IMS that selectively interacts with Arg peptide fragments of the protein. These Arg peptide fragments can be separated/resolved from the Lys peptide fragments and can be further identified by having an MS or other analytical instrument connected to the IMS.

In another set of embodiments of the present invention at least one targeted molecular geometry in at least one component of the sample to be resolved has at least one chiral center including one or more functional groups. The chiral center(s) can be: part of, attached to, adjacent to, removed from, and any combinations thereof, the functional group(s). At least one chemical modifier is added to the drift gas that interacts selectively with the targeted molecular geometry to be resolved. The chiral center(s) can set the molecular geometry to have a specific interaction with the chemical modifier, which may or may not include a chiral center(s).

In yet another set of embodiments of the present invention at least one immobilizing agent can be added to the sample to rigidify with: either the targeted chemical and/or biological molecules or the impurities and/or interferences in the sample, or both. The immobilizing agent can be added to the sample at various stages of the process of introducing the sample to the IMS. Some non-limiting examples of adding the immobilizing agent to the sample are: prior to adding the sample into the ionization region, while the sample is in the ionization region, after the sample has been ionized. As the molecules increase in molecular complexity (size, number of stereogenic centers, number of chiral centers, number of functional groups, etc) more conformations are possible due to the flexibility of the molecule, which can thus adopt multiple different conformations while traveling down the drift tube. By rigidifying the molecules, the immobilizing agent can limit the possible conformations of the components of the sample. The immobilizing agents include, but are not limited to: chemical and/or biological molecules, inorganic compounds, organic compounds, metals, minerals, macromolecules, polymers, biopolymers, nucleotides, proteins, carbohydrates, lipids, macrocycles, and nanotubes. Fewer conformations of the components of the sample can enhance resolution/separation owning to more specific interactions with the modifier. A non-limiting example of the process would be to form a [metal-sample component] complex prior to ionization and then perform the mobility analysis while adding at least one modifier to the drift gas. Interactions between the [metal-sample component] complex and the modifier would be identified by different drift times of the molecules on a detector. The detector may be a: mass spectrometer, faraday plate, CCD, high pressure multiplier, any transducer that produces a signal proportional to the number of ions at the detector, but not limited to only these.

Many different metals are envisioned to be used for forming a [metal-sample component] complex, including: Alkali metals (Li, Na, K, Rb, Cs, Fr), Alkaline earth metals (Be, Mg, Ca, Sr, Ba, Ra), Transition metals (Sc, Ti, V, Cr, Mn, Fe, Co, Ni, Cu, Zn, Y, Zr, Nb, Mo, Tc, Ru, Rh, Pd, Ag, Cd, Hf, Ta, W, Re, Os, Ir, Pt, Au, Hg, Rf, Db, Sg, Bh, Hs, Uub), Metalloids (B, Si, Ge, As, Sb, Te, Po), other metals (Al, Ga, In, Sn, Tl, Pb, Bi), Lanthanides (La, Ce, Pr, Nd, Pm, Sm, Eu, Gd, Tb, Dy, Ho, Er, Tm, Yb, Lu), Actinides (Ac, Th, Pa, U, Np, Pu, Am, Cm, Bk, Cf, Es, Fm, Md, No, Lr), but not limited to only these. The metals could be used with various counter ions and/or combinations of counter ions including: Halogen (Cl, Br, I, F), acetate, nitrile, hydrate, acetylacetonate, carbonate, hydroxide, methoxide, ethoxide, propoxide, nitrate, oxide, perchlorate, selenide, sulfate, sufide, triflate, thiocyanate, but not limited to only these.

An ion mobility spectrometer can recognize separate structural (constitutional) or conformational isomers since they have a different geometric appearance but exactly the same mass. Ions with the same mass but with different collision cross sections have different mobilities. If different conformational isomers of the same compound are analyzed, the isomer with the smallest geometric cross section will have the highest ion mobility. It has been shown that tightly folded proteins have a smaller geometric cross section than the unfolded conformation of the same protein and the unfolded conformation therefore has a longer travel time to the detector. In small molecules, less than 500 MW, the free-energy difference between conformers (conformational free energy) can be a small or large rotational energy barrier depending on the molecules functional groups. In addition, functionality within the molecule can influence the molecules preferred conformation. For example, an intramolecular hydrogen bonding of the compound shown in FIG. 13 produces a conformationally restricted molecule.

One embodiment of this invention is to rigidify the molecules (limit the number of conformations) by adding an immobilizing agent to the sample prior to ionization. A non-limiting example is shown in FIGS. 14A-B, where a metal is added to the unrestricted molecule in FIG. 14A, which produces a metal complex as shown in FIG. 14B. The metal coordination complex can be formed by the interaction of atoms to the metal by action of one or more of: a metallic bond, a coordinate covalent bond, a ionic bond, or a combination of these, but not limited to only these interactions. By adding a metal to bind to functionality in a molecule which contains at least one chiral center, this would limit the molecule's conformations and optimal enantiodiscrimination would occur by the chemical modifier which may contain one or more chiral centers. One non-limiting example is shown in FIGS. 15A-15B. FIG. 15A shows a component of the sample with 2 chiral centers and multiple possible conformations. By adding a metal to the component before it is ionized in the IMS, the conformation shown in FIG. 15B may predominate and produce a rigid structure for optimal chemical modifier interaction.

In one aspect of the gas phase separation/resolution method is using an immobilizing agent to stabilize the gas phase structure of analytes in order to enhance the gas phase separation. In variety of embodiments, a reagent that can frame (affix) the higher order structure of a gas phase analyte molecule is used to achieve well-defined gas phase mobility of the analytes. Forming complexes with metals and/or other molecules is illustrated above as a non-limiting example of this method. In alternative embodiments, the analytes can be first affixed on a carrier, the carrier reagent can be molecule, a particle, nanotube, or macromolecules, and then separate the analytes with different characteristics via above described SSIMI method. In some cases, when the analyte is affixed, certain active sites of the analytes may be accessible allowing designed gas phase interaction to occur in a well-defined manner. During the execution of this method, the interaction between the analytes and the carriers could either be permanent or in transient time. The immobilizing agents having a spatial structure that is used to reduce the degree of freedom of intramoleuclar movement of the component in the samples. The immobilizing agents limit conformational changes to the component of the sample such that the modifier interacts with a defined three dimensional structure of the component of the sample.

A structure selective resolution method can comprise: adding at least one immobilizing agent to a sample, which rigidifies at least one component of the sample; ionizing and providing the sample with the immobilizing agent to an ion mobility based spectrometer; adding at least one chemical modifier that interacts selectively with the component and/or the associated immobilizing agent of the sample; providing energy in addition to the thermal energy at a given temperature to influence the separation of the components in the sample; and resolving the component from other components of the sample based on their measured ion mobility characteristics. The immobilizing agents include, but are not limited to: chemical and/or biological molecules, inorganic compounds, organic compounds, metals, minerals, macromolecules, polymers, biopolymers, nucleotides, proteins, carbohydrates, lipids, macrocycles, and/or nanotubes.

Figure 17A:
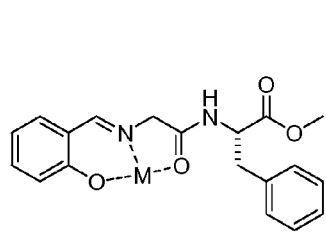
Figure 17B:
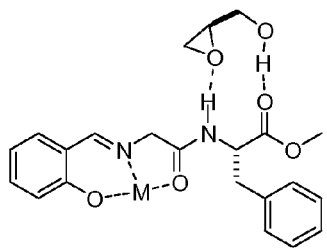
Figure 17C:
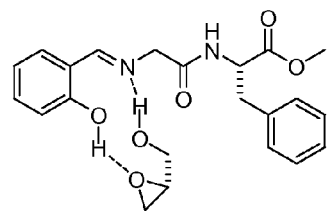
Figure 18:
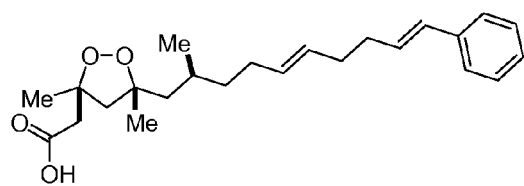
FIG. 18 shows a biologically active peroxide, a transforming agent, and a chemical modifier.
Figure 18:
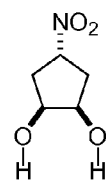
Figure 18:
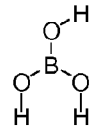
Figure 19:
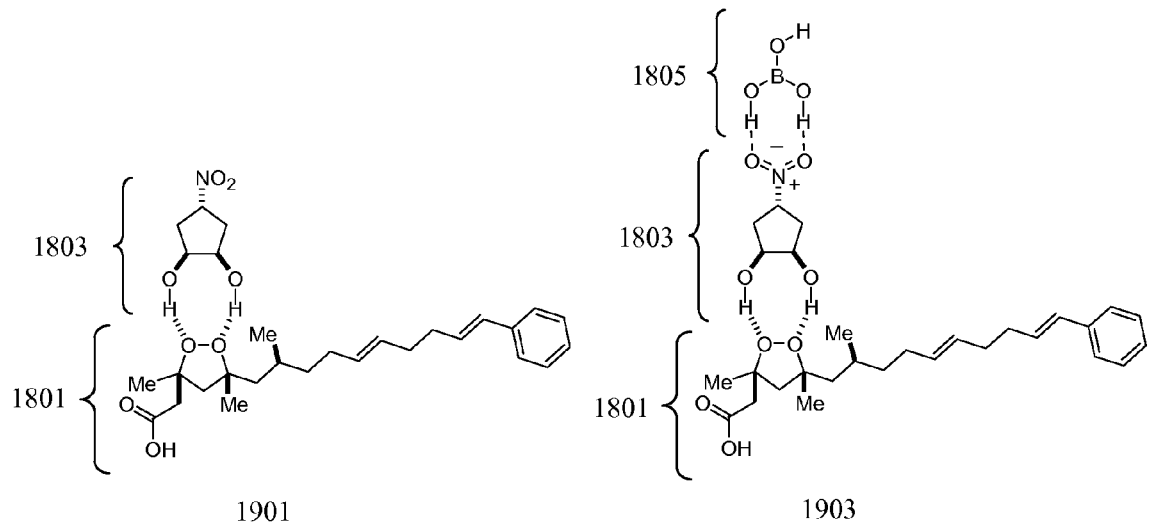
FIG. 19 shows the chemical modifier bound selectively to the complex 1901 through the nitro functionality found on the transforming agent 1803 as complex 1903.

Another embodiment of this invention is to add at least one transforming agent to a sample, which bonds/binds to at least one component of the sample. The transforming agent can be added to the sample at various stages of the process of introducing the sample to the IMS. Some non-limiting examples of adding the transforming agent to the sample are: prior to adding the sample into the ionization region, while the sample is in the ionization region, after the sample has been ionized. At least one chemical modifier is added to the IMS that interacts selectively with the component of the sample and/or transforming agent which resolves/separates the component from other components of the sample based on their measured ion mobility characteristics. The transforming agent is designed to selectively bond/bind to at least one functional group of the component to block these functional group(s) from interactions with the chemical modifier and/or is designed to interact with the chemical modifier after selectively bonding/binding to at least one functional group of the component. The first use of the transforming agent described above would be similar to how a protecting group is used in organic chemistry reactions to block or protect a functional group while reactions are carried out on other functional groups on the compound. As a non-limiting example, a component of the sample has a non-chiral bonding/binding functionality as well as a chiral bonding/binding functionality. In this situation, the non-chiral binding pocket/functionality could be avoided by a chiral chemical modifier and therefore enhance chiral recognition if a transforming agent was added to the sample which blocks the non-chiral binding pocket/functionality from interaction with the chiral chemical modifier. This would occur by selectively interacting with the sites of the targeted functionality near the chiral center of the molecule. A non-limiting example is shown in FIG. 16, where the molecule has one chiral center and multiple possible conformations. If a metal is added to the molecule it may bind in the manner shown in FIG. 17A, allowing a chiral modifier to interact in the vicinity of the molecule's chiral center, shown in FIG. 17B. By adding a complexing metal to the component of the sample, before the enantiodiscrimination process, the desired chiral recognition site is bound instead of unfavorable binding pocket(s) and/or functional group(s). FIG. 17C shows the chiral modifier interacting with a non-chiral binding pocket instead of interacting in a vicinity that is near the chiral center of the molecule. Described below is a non-limiting example for the second use of the transforming agent whereby the transforming agent is designed to interact with the chemical modifier after selectively bonding/binding to at least one functional group of the component. In this non-limiting example, a biologically active peroxide such as epiplakinic acid D 1801 (a component of the sample) shown in FIG. 18 does not contain functionality that interacts selectively with the chemical modifier 1805. Therefore, a transforming agent 1803 is added to the sample and bonds/binds to the peroxide functionality of epiplakinic acid D 1801 to some degree as shown in FIG. 19 as a complex 1901. The nitro functionality found on the transforming agent 1803 furnishes a handle to bond/bind with the chemical modifier 1805. FIG. 19 shows the chemical modifier bound selectively to the complex 1901 through the nitro functionality found on the transforming agent 1803 as complex 1903. In the above example the transforming agent 1803 bonds/binds to the epiplakinic acid D 1801 (the component of the sample) through non-covalent bonding (hydrogen bonding), however this method could also utilized by using transforming agents that covalently bonds to the component of the sample via a synthetic transformation (organic reaction).

Another embodiment of this invention is to use the immobilizing agent and transforming agent as one agent. In this case the agent rigidifies at least one component of the sample and the chemical modifier interacts selectively with the agent that rigidified the component of the sample. This is similar to the above described second use of the transforming agent, although in this case the transforming agent also rigidifies the component of the sample.

In yet another embodiment of this invention is to use the immobilizing agent and transforming agent together. In this case, the immobilizing agent added to the sample rigidifies at least one component of the sample and the transforming agent which is also added can be used to selectively bond/bind to at least one functional group of the component to block these functional group(s) from interactions with the chemical modifier and/or is designed to interact with the chemical modifier after selectively bonding/binding to at least one functional group of the component.

A structure selective resolution method can comprise: adding at least one transforming agent to a sample, which bonds to at least one component of the sample; ionizing and providing the sample with the transforming agent to an ion mobility based spectrometer; adding at least one chemical modifier that interacts selectively with the component of the sample and/or the transforming agent; providing energy in addition to the thermal energy at a given temperature to influence the separation of the components in the sample; and resolving the component from other components of the sample based on their measured ion mobility characteristics. The transforming agent can be designed to selectively bond to at least one functional group of the component to block at least one functional group from interactions with the chemical modifier. The transforming agent can be designed to: interact with the chemical modifier after selectively bonding to at least one functional group of the component, and/or also rigidifies the component of the sample. In addition to adding a transforming agent, the addition of at least one immobilizing agent to a sample, which rigidifies at least one component of the sample can also be done.

In yet another aspect of the present invention one or more internal and/or external standards can be used to calibrate the ion mobility base spectrometers by defining and/or knowing the degree of the interaction between modifiers and ions. Ion mobility charateractics of the calibrants, such as the drift time, in the ion mobility spectrum can be used to verify the system readiness. The standards can be a substance that has known degree of interaction with the modifiers. With the understanding of the relationship the ion mobility behavior of a sample component under a variety of operating conditions, such as, but not limited to, temperature, pressure, humidity, electric field, flow rate, the kind of modifiers, modifier concentration, etc., a calibration standard can be used to determine the operating condition changes and predict associated change of ion mobility characteristics, such as ion drift time. In a variety of embodiments, the calibration method may consist of introducing a first calbrant and measuring a first ion mobility characteristic; introducing a second calibrant and measuring the second ion mobility characteristic; using measured ion mobility characteristics to determine proper instrument operating parameters, such as, but not limited to, temperature, pressure, humidity, electric field, flow rate, the kind of modifiers, modifier concentration, etc. The system calibration process may also include using the calibration parameters that correlate known and unknown instrument operational condition to correct data obtained under unknown instrument conditions. Such correction can either been done on-the-fly or after the data is obtained. In many embodiment, the correction can be achieved using system control and data acquisition software and/or data analysis software. In practice, the first and second calibrant can be introduced to the instrument either sequentially or simultaneously. For above described calibration process, one or more calibrants are used.

The term ion mobility separator, and ion mobility spectrometer, and ion mobility based spectrometers are used interchangeably in this invention, often referred to as IMS, including time-of-flight (TOF) IMS, differential mobility spectrometers (DMS), field asymmetric ion mobility spectrometers (FAIMS) and their derived forms. A time of flight ion mobility spectrometer and their derived forms refers to, in its broadest sense, any ion mobility based separation device that characterize ions based on their time of flight over a defined distance. A FAIMS, a DMS, and their derived forms separate ions based on their ion mobility characteristics under high values of normalized electric field.

In a general sense, ion mobility spectrometers are currently used to separate components of a sample by differentiating their ion mobilites and/or ion mobility differences under given electric field conditions. The present invention describes differentiating components in a sample in an IMS using at least one additional property of the components besides their ion mobility and/or ion mobility differences.

Under low electric field conditions, the ion mobility is related to reduced mass, collision cross section (size and/or shape), and charge state of the components and the components are differentiated from each other by the time it takes the components to travel in the drift media under influence of electric field. In one embodiment, the present invention describes separating components in a sample in an IMS simultaneously using at least one additional property of the components other than the ion mobility, i.e. reduced mass, collection cross section (size and/or shape) and charge state of the components to enhance separation and/or resolution of the sample. Separation based on the additional property is realized by introducing modifier into the drift media of the IMS; such modifier selectively interacts with one or more component in the sample based on the additional property of the sample component. The additional property of a substance (component of the sample) can be utilized to enhance separation and/or resolution of the sample components may include, but not limited to: reactivity, polarity, hydrophobic and/or hydrophilic properties, size-exclusion properties, structure selective affinities, acidity and or basicity, pH, energy level, phase of matter, color, magnetism, biological activity, boiling point, etc.

Figure 20:
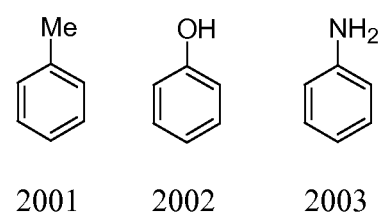

One embodiment of this invention is to add at least one modifier to the drift gas that interacts selectively, to some degree, with one component over the other(s) by the inherent polarity of the component. In this non-limiting example, a modifier(s) would be added to the drift gas that targets the polarity of the components. Modifiers with similar molecular property would be added to the drift gas, so that the modifiers can only cause similar ion mobility changes without considering the additional property, in this case, the polarity. By using these modifiers, the additional properties (polarity) of the sample component is used to interact with the modifier, thus affects the separation in the IMS. FIG. 20 shows three modifiers varying in polarity that are used to affect component separation and have a very similar size. Modifier 2001 is the least polar, modifier 2002 is more polar, and modifier 2003 is the most polar. Each modifier could be added separately or together as a mixture. The amount of the modifiers could be adjusted on-the-fly as a gradient. The method of adding this modifiers may be involve adding certain amount of modifiers forming constant concentration of modifier in the drift media; the ion mobility measurement is conducted under a constant modifier condition. Alternatively, modifier concentration could be increased or decreased while a sequence of ion mobility measurements is conducted; the gradient of modifiers can be controlled by introducing less polar modifier to more polar modifier, or more polar to less polar to the drift gas.

Given two components in a sample having same ion mobility in a drift media, but different polarity, the polar component has a stronger interaction with the polar modifier when modifier is added into the drift media. Consequently, the less polar component travels faster through the drift region of the IMS, thus the two components can be separated. In an alternative embodiment, as the drift media consists of drift gas and modifier(s), the drift gas can also be changed to enhance the separation along with the modifier(s). For example, choosing a less polar drift gas would enhance the interaction between the polar component and the polar modifier since the interaction would be magnified.

Figure 21:
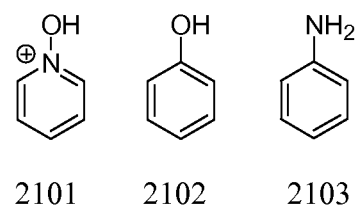
FIG. 21 shows three modifiers varying in polarity that are used to affect component separation and have a very similar size.

An alternative embodiment of this invention is to add at least one modifier to the drift gas that interacts selectively, to some degree, with one component over the other(s) by the inherent pH of the component. In this non-limiting example, a modifier would be added to the drift gas that targets the additional properties of the components, i.e. acidity or basicity of the components. Modifiers having similar mass and size would be added to the drift gas, so that the conventional collisions of the components with the different modifiers used would not affect a mobility difference. FIG. 21 shows three modifiers varying in pKa that are used to affect component separation and have very similar mass and size. Modifier 2101 has a $pK_a$ of 0.7, modifier 2102 has a $pK_a$ of 10, and modifier 2103 has a $pK_a$ of 41. The modifiers could be added separately, as a mixture, or as a gradient (lower pKa to higher pKa or higher pKa to lower pKa) to the drift gas.

Another embodiment of this invention is to add at least one modifier to the drift gas that interacts selectively, to some degree, with one component over the other(s) by another additional property of the component, i.e. surface tension. In this non-limiting example, a micelle could be added to the drift gas that targets the interfacial tension of the component. A molecule in contact with a neighbor is in a lower state of energy than if it wasn't in contact with a neighbour. The interior molecules all have as many neighbours as they can possibly have. But the boundary molecules have fewer neighbours than interior molecules and are therefore in a higher state of energy. For the component to minimize its energy state, it must minimize its number of boundary molecules and must therefore minimize its surface area. In addition, the modifier could be a surfactant, phospholipid, or a colloid. This interact may be come significant while conducting ion mobility measurement in liquid phase or high pressure conditions (e.g. several atmospheric pressures)

The present invention also describes method and apparatus to add energy to the components of the sample to be separated to enhance separation in IMS. The method of tuning the ion energy with an energy source in-conjunction with adding a chemical modifier to the drift gas and/or adding a shifting reagent may enhance the interaction of the chemical modifier and/or shifting reagent with the ions thereby improving the overall separation of the sample ions.

Figure 22:
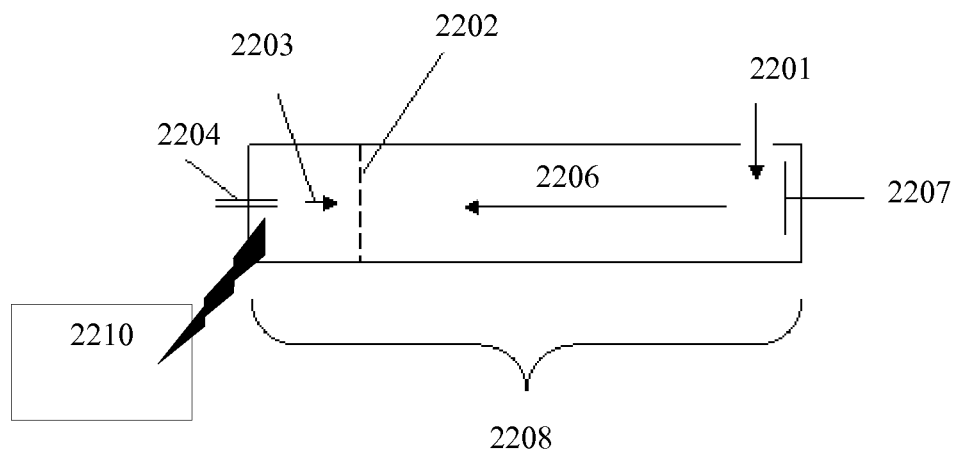
FIG. 22 shows three modifiers varying in pKa that are used to affect component separation and have very similar mass and size.

The present invention uses an energy source to supply energy to ions or neutral molecules in an ion mobility based spectrometer as a means to optimize the interaction between ions and neutral molecules to achieve optimal separation in these devices. Not only the neutral gas (drift gas), but at least one chemical modifier and/or adding a shifting reagent is also supplied to the spectrometer. When utilizing a chemical modifier, the chemical modifier undergoes a gas phase interaction with the ions to be separated. The ion energy is tuned to achieve optimal separation for the given ions in the media (including both drift gas and chemical modifier). The ion energy level could be scanned from low to high during the separation process. For example, acquiring one ion mobility spectrum under one energy level, and then acquiring another ion mobility spectrum at a different energy level; the process could be repeated until maximum ion mobility based performance can be achieved. The energy source can supply energy to the ions in any region of the spectrometer, the ionization, reaction, and/or drift. As a non-limiting example, FIG. 22, shows the drift media 2201 is introduced into the IMS in drift region and the shifting reagents could be added to the IMS with the drift media and/or directly into the ionization region, reaction region, or other section of the IMS. Alternatively, the shifting reagents could be premixed with the sample before introducing to the IMS. In a time of flight IMS, the drift tube is separated ionization/reaction region and drift region by an ion gate 2202. Sample components are ionized before the ion gate 2202 and then guided into the drift region under influence of electric field. The ion trajectory 2203 and the drift media flow 2206 in opposite directions. With an energy source 2210, sample components and/or drift media in the drift tube 2208 are tuned at an energy level that is suitable for the ion mobility based separation. The separated sample components are collected or detected at the end of drift tube on collector 2207.

Figure 23:
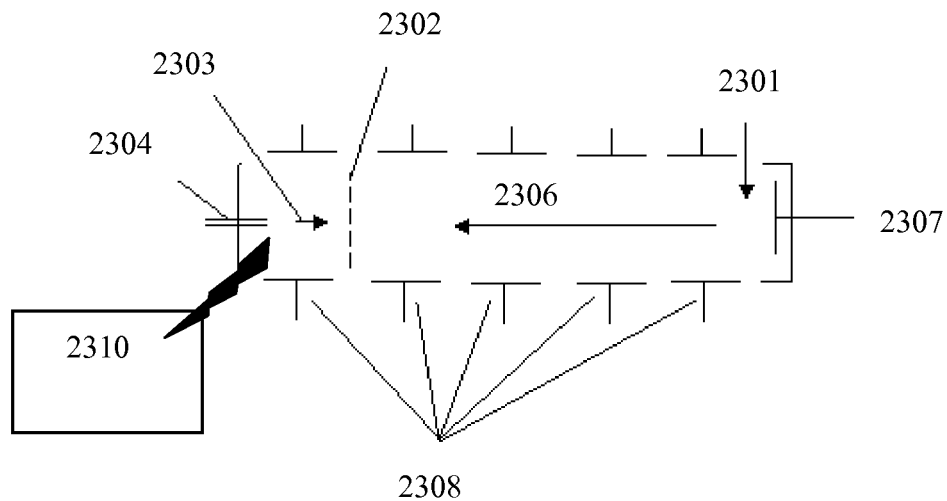
FIG. 23 shows adding energy to either the components or the drift media.

As a non-limiting example, the ions energy in the ion mobility based spectrometer can be tuned by supplying an RF electric field to the ions as described in patent application Ser. No. 12/026,192. By adjusting the frequency, amplitude and/or other parameter of the RF waveform, the ion energy is tuned while being separated either based on their static ion mobility in a time of flight ion mobility spectrometer or ion mobility variation in a field asymmetric ion mobility spectrometer. As a non-limiting example, FIG. 23, shows a TOF-IMS using electrodes that are biased with both DC and RF fields. Similarly, the drift media 2301 is introduced into the IMS in drift region. In the time of flight IMS, the drift tube is separated into ionization/reaction region and drift region by an ion gate 2302. Sample components are ionized before the ion gate 2302 and then guided into the drift region under influence of electric fields. In this case, a RF electric field is added to the drift tube (ionization and/or drift region) through electrodes 2308 to maintain the ions at a given energy level (the apparatus and methods of adding RF electric field to an IMS is described in U.S. patent application Ser. No. 12/026, 192). The ions travel through the drift media flow 2306 with a direction of 2303. In one embodiment, an energy source 2310 can be used with the RF electric field either simultaneously or as an alternative energy source to achieve the performance goals. When used simultaneously, the additional energy source 2310 and RF electric field may be used to energize difference sample components, neutral molecules that are associated with the sample components, shifting reagents, and/or drift media. As a non-limiting example, the RF electric field can be used to keep the sample components from clustering with the surrounding neutral molecules (such as water), and the additional energy source 2310 is tuned to achieve separation based on the component (or the interaction product of component and shifting reagent)-drift media interaction. Alternatively, the additional energy source 2310 using a laser beam that is guided to inside a drift tube with an bandwidth that selectively heat up the water molecule, thus prevent them from clustering, and the RF electric field maintains the sample component ions at a energy level that is suitable for the component (or or the interaction product of component and shifting reagent)-drift media interaction achieving the ion mobility based separation. The separated sample components are collected or detected at the end of drift tube on collector 2307.

A ion mobility based separation method can comprise: adding a shifting reagent to a sample which interacts with at least one component of the sample; separating at least one component of the sample in a drift media based on their measured ion mobility characteristics; providing energy in addition to the thermal energy at a given temperature to one or more of: the components and/or the shifting reagent and/or the drift media influencing the separation of the components in the sample; and tuning the energy level to alter the degree of separation of the components. The shifting reagent can be chemoselective. The shifting reagent can be chemoselective for a peroxide functional group. The drift media can comprise: one or more of noble drift gas, interactive drift gas, and/or modifier in a known ratio that is in a range of zero to one hundred percent. The energy can be generated using means of a range of electromagnetic energy, in particular in the visible, infrared, microwave radio range. The energy can be from a source comprising a laser and/or radio frequency electric field. The energy can also be used to prevent neutral molecules from clustering with sample components prior to and/or during the separation in the drift media.

A ion mobility based spectrometer can comprise: a shifting reagent added to a sample; a drift media wherein at least one component of the sample is separated based on their ion mobility characteristics; one of more energy sources that provide energy in addition to the thermal energy at a given temperature to one or more of: the sample, and/or the shifting agent, and/or the drift media influencing the separation of the components in the sample; and the energy level can be tuned to alter the degree of interaction between: the sample components, and/or shifting reagent, and/or the drift media for the separation of the components. The shifting reagent can be chemoselective. The shifting reagent can be chemoselective for a peroxide functional group. The drift media can comprise: one or more of noble drift gas, interactive drift gas, and/or modifier in a known ratio that is in a range of zero to one hundred percent. The energy can be generated using means of a range of electromagnetic energy, in particular in the visible, infrared, microwave radio range. The energy can be from a source comprising a laser and/or radio frequency electric field. The energy can also be used to prevent neutral molecules from clustering with sample components prior to and/or during the separation in the drift media.

Unless otherwise specified in this document the term "shifting reagent" (includes the commonly used terms: dopant and ionization reagent) is intended to mean single or plurality of chemicals and/or biological(s) which to certain degrees selectively interacts with at least one component of the sample. The shifting reagent can be a immolizing agent and/or a transforming agent. The shifting reagent interaction with at least one component of the sample, may include: covalent bond, ion-molecule reactions, clusters (clustering), ionic bond, salt bridge, cation-pi interaction, hapticity, polar covalent bond, coordinate covalent bond, metallic bond, disulfide bond, peptide bond, phosphodiester bond, or combinations of these, but is not limited to only these. The shifting reagent may involve forming a cluster with at least one component of the sample. The shifting reagent may involve a derivatization of the component of the sample via a permanent covalent bond, such as that used in covalent synthesis. The shifting reagent may involve interacting in the gas phase with at least one component of the sample transferring protons or electrons to component molecules and forming component ions. In addition, the shifting reagent may have one or more chiral center(s).

The shifting reagent can be added to the sample prior to ionization, during ionization of the sample, or after the sample has been ionized. In particular, the shifting reagent can be added to: the drift gas, the sample, or the ionization region of the analytical instrument. The shifting reagent can be added to the sample prior to ionization and/or directly introducing them into the reaction region of the drift tube of time of flight type of IMS. In case of other type of ion mobility based spectrometer, the shifting reagent could be added into the carrier gas before or during separation.

Certain embodiments of the present invention involve a series of shifting reagents that selectively interact with a targeted functional group of biological molecules, pharmaceutical drugs, small molecules, chemicals, chemical agents, or explosives resulting in a structure selective based drift time shift in the IMS. A shifting reagent can selectively increase and/or decrease the drift time of a class of components in the sample that has a common targeted functional group. The targeted functional group can come from the previously listed functional groups. The shifting reagent can be chemoselective. This chemoselectivity is the preferential reaction of a shifting reagent with one of two or more different functional groups. A reagent has a high chemoselectivity if reaction/interaction occurs with only a limited number of different functional groups. For example, sodium tetrahydroborate is a more chemoselective reducing agent than is lithium tetrahydroaluminate. In the following non-limiting example, the shifting reagent's targeted functional group is the nitro functional group. The drift time of nitro based explosives such as TNT, RDX, and Nitroglycerine all are moved away from their original drift time eliminating common interference problems in IMS. FIG. 2 shows an ion mobility spectrum resulting from a laboratory test in which a known amount of TNT was introduced to the system. During the course of detection, multiple peaks were detected and only one of them is directly related to the component TNT 203. Another predominant peak 201 is the instrument background ion. Note that there is significantly less or no interference existing in the relatively long drift time region 207. In this particular example, the several other interferant peaks distributed between these two peaks; most of them are in the low drift time range. In addition, this spectrum was acquired in a laboratory environment whereby field samples commonly show more complex ion mobility spectra. Unfortunately, most nitro based targeted analytes have very similar ion mobilities as the interferants. The nitro based explosives have a drift time in the region as shown within the 205 dashed line box in FIG. 2. In this region, detection windows and thresholds are a compromise between sensitivity and false alarm rate and significantly limit detecting low levels of explosives and make it impossible to detect explosives. Instead of using the chemical modifiers described in the previous sections, a shifting reagent can be used to selectively adjust the drift time of components in a sample of interest, to a desired region of the IMS spectrum where few or no interfering chemicals exist. As FIG. 2 illustrates, if the drift time of all nitro based explosives is shifted the long drift time range 207 dashed line box, there is very low probability for interference; the detection threshold could be reduced to a much lower level.

In addition to selectively increasing the drift time of a class of components in the sample that has a common targeted functional group, the shifting reagent can be used to target a common functional group with an additional feature of that particular component of the sample that the shifting agent has specificity. The additional feature may include: electronics of the molecule (i.e. lone pairs, electron distribution over the molecule, +/− charge distribution), steric hindering effects, bond connectivity, chemical affinity, but is not limited to these. The following example is non-limiting. For example, a sample may have 3 components (A, B, C) that have a nitro functional group, a component (D) with a alcohol, and a component (E) with an aniline. A shifting reagent is added to the sample that targets nitro functional groups. Therefore, components (A, B, C) should have their drift times altered, either shorter or longer in time. However, in this example, component (B) is an aliphatic connected nitro functional group. Components (A & C) are both aromatic connected nitro functional groups. The shifting reagent has specificity for aromatic nitro functional groups. Therefore only components (A & C) have their drift times altered. The additional feature in this example is bond connectivity.

In a variety of embodiments, the shifting reagents can be added to an IMS to convert analytes of interest into a new compound or cluster via covalent or non-covalent bonds. The shifting reagents could be added to the sample prior to introducing to the IMS or added to the ionization, reaction (desolvation), and/or drift (analyzer) region of the IMS. The shifting reagents could be mixed with the sample in solution and/or gas phase.

By measuring the ion mobility characteristic of the product ions generated by mixing the analytes and known shifting reagent, the analyte could be identified. Additional information related to the mixed product can also be obtained thereby assisting the identification of the analytes. This information may include the properties that are related to the analyte and shifting reagent interaction, such as molecular structure, reactivity, charge affinity, etc., which could be specific when the shifting reagents are selected to interact with a variety of analytes differently.

The measured ion mobility characteristics of analyte ions before and after interacting shifting reagent can be used to construct a multidimensional ion mobility profile. In one embodiment, the first ion mobility characteristic (in case of time of flight type IMS, drift time can be used; in case of FAIMS or DMS, compensation voltage can be used) of the analyte is measured in the first IMS and then at least a portion of these ions are subsequentially introduced into the second IMS, wherein one or more shifting regents are added, wherein the second ion mobility characteristics is measured. The first and second ion mobility characteristics are used to construct ion mobility profile for compound identification.

A method for detecting samples using an ion mobility based spectrometer includes ionizing at least one compound of interest in a sample in an ionization source; separating and detecting ions of the compound of interest in a first drift chamber; adding a shifting reagent to interact with a portion of the ions and conveying the ions from the first drift chamber into a second drift chamber; and confirming the ions are the compound of interest in the second drift chamber using second measured ion mobility.

In a variety of embodiments, there may be a region between the first drift and the second drift chamber allowing the shifting reagents to interact with ions of the compounds of interest.

In one embodiment, the shifting reagents are ionized prior to interacting with the analytes. In this case, the shifting reagents are used as the reactant that ionize and covert analyte into a new product ion. In many examples of this practice, the shifting reagents are used to alter the ionization chemistry. In an alternative embodiment, the shifting reagents are not involved in the ionization process, but interact with analytes that have been ionized. In this case, the resulting product ions have a different drift time (ion mobility characteristics) compared to the drift time of analytes alone.

A multidimensional ion mobility spectrometer (MDIMS) may be constructed in orthogonal and/or tandem arrangement. In various embodiments of the MDIMS, it is understood that a preferred embodiment is to arrange the drift axis of each dimension in orthogonal geometry, however, the drift axis can be arranged in parallel, anti-parallel or with an angle in between to achieve similar results.

Instead of drift time of analytes in a single dimension drift chamber, in a two-dimensional IMS system, two drift chambers can be used to generate a two-dimensional mobility profile of both positive and negative ions simultaneously. For chemical identification purpose, an analyte has drift times in the first and second drift tube chamber (under a calibrated conditions) will fit in the ion mobility profile resulting in a positive identification. The two-dimensional ion mobility data provides higher confidence in chemical detection. As a practical operational approach, first dimension mobility spectra can be acquired for higher throughput screening; when peaks are detected in the explosive detection window from the first drift chamber they are then brought into the second drift chamber for confirmation. The method further comprising measuring ion mobilities of ions in a plurality of drift chambers that could be supplied with the same of difference drift media; constructing a multidimensional ion mobility profile from the measurements; and identifying chemical species based on the multidimensional ion mobility profile.

In various embodiments, for example, suppose a first drift dimension is used as a screen scan, and a compound of interest (e.g., TNT) is detected as potentially present. To further confirm that the ion responded in the detection window (time window) is indeed the compound of interest, one can selectively extract the peak in that detection widow into the second dimension for further separation and detection; whereby the second dimension may be provided with one or more shifting reagents and/or chemical modifiers. From the second dimension, ions that fall into a selected window can be extracted into a third dimension whereby the third dimension may be provided with one or more different shifting reagents and/or chemical modifiers. This process can be repeated until the ion current is exhausted if so desired.

In a MDIMS, the shifting reagents could be either added to the lower dimension drift tube (e.g. first drift tube) or higher dimension drift tube (e.g. second drift tube). In the case where the shifting reagents are added to the lower dimension drift tube, the ions of interest could be converted before entering the second drift tube by removing the shift reagents from the ions. The removal could be, but not limited to, a declustering process, a dissociation process, a fragmentation process.

In an alternative embodiment, the shifting reagents are added to form a product ion(s) that could be separated better in the IMS as a result of the enhanced interaction between the product ions and the drift media. For example, the resulting product ions of shift reagents and the analytes may have an additional polar functional group that readily interacts with a polar drift media.

The following examples are non-limiting. The targeted functional group is a representative example of how the shifting reagent can be used to shift the drift times of the component(s) of the sample that have the targeted functional group.

Detecting nitro based explosives can exhibit high false alarm rates and/or not be detected due to their short drift time detection window. To alter (increase and/or decrease) their drift times, several interaction mechanisms can be used to selectively adjust the drift time of components in a sample of interest, to a desired region of the IMS spectrum where few or no interfering chemicals exist.

Nitro based explosives include, but are not limited to: TNT, RDX, HMX, Tetryl, PETN, Nitroglycerin, EGDN, ammonium picrate (Explosive D), 2,4,6-trinitrophenol (picric acid), 2,4,6-trinitroaniline (MATB), 1,3-diamino-2,4,6-trinitrobenzene DATB), 1,3,5-triamino-2,4,6-trinitrobenzene (TATB), 2,2',4,4',6,6'-hexanitrostilbene (HNS), 2,2',4,4',6,6'-heanitrodiphenylamine (dipicrylamine), diethylene glycol dinitrate (DEGN), triethylene glycol dinitrate (TEGN), nitrocellulose (NC), mannitol hexanitrate (MHN), ethylene diamine dinitrate (EDDN), monoethanolamine dinitrate, ethylenedinitramine (EDNA), diethylnitramine dinitrate (DINA), nitroguanidine, dinitroglycoluril (Dingu), tertranitroglycoluril (Sorguyl), 1,3,3-trinitroazetidine (TNAZ), hexanitrohexaazaisowurtzitane (CL-20) or any combinations of these explosives, in particular: Amatol, Ammonal (Minol), Composition A-3, Composition B, Composition C-4, Cyclotol, DBX, Detasheet, H-6, HBX-1, Hexyl, LX-10, LX-17, Octol, PBX-9404, PBXN-107, PE 4, Pentolite, Picratol, PTX-1, PTX-2, Semtex-H, Tetrytol, Torpex, Trigonol, Tritonal, Dynamite, Dynamite 3, Gomme A, Wetter-Carbonit C.

Figure 24A:
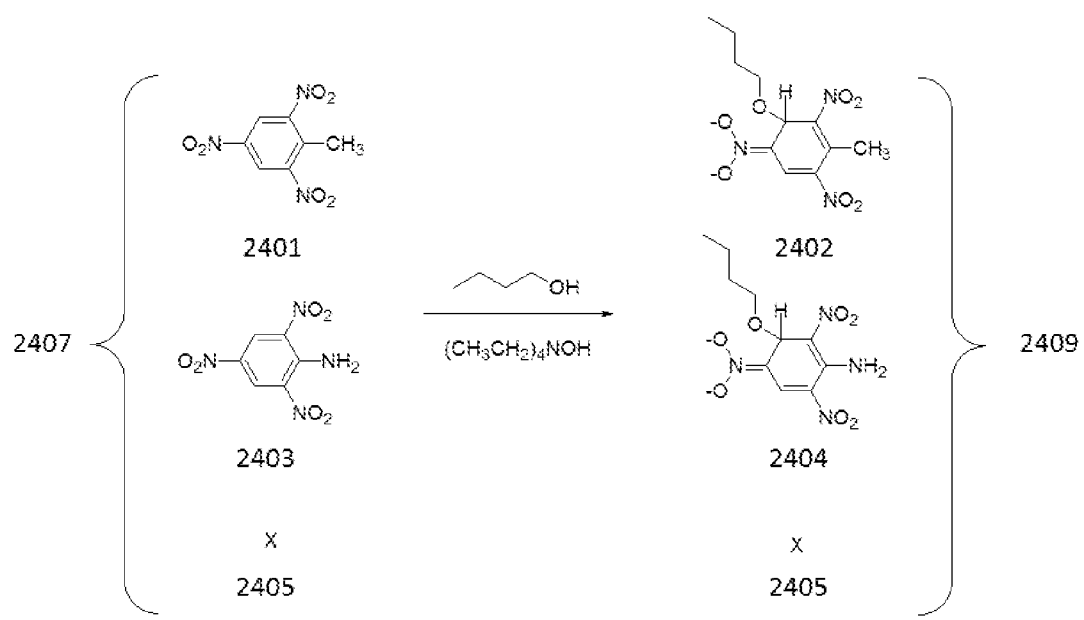
FIG. 24 shows adding an RF energy and an additional energy source.
Figure 24B:
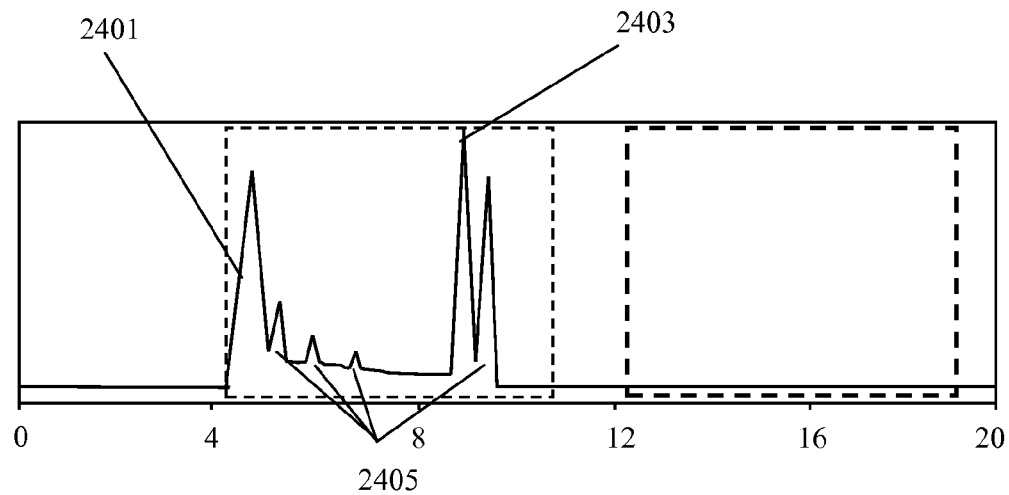
Figure 24C:
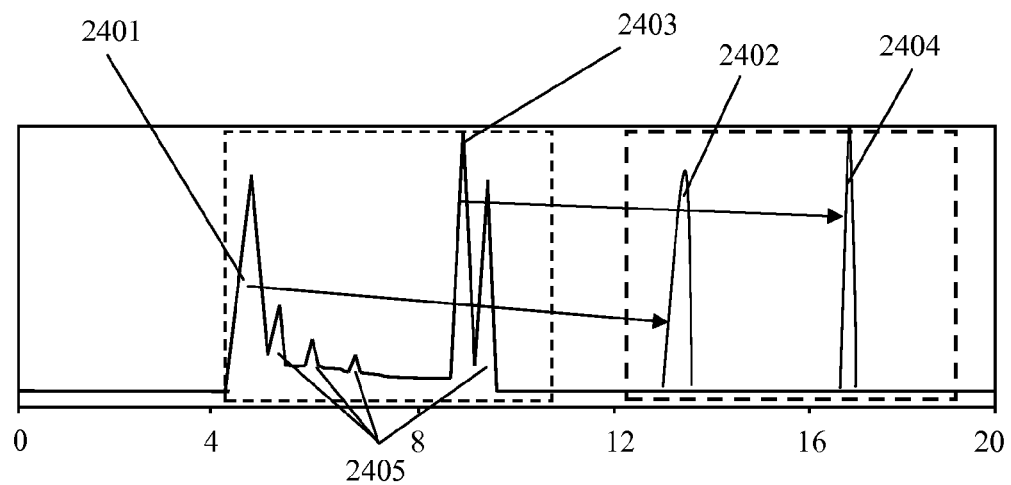
Figure 24D:
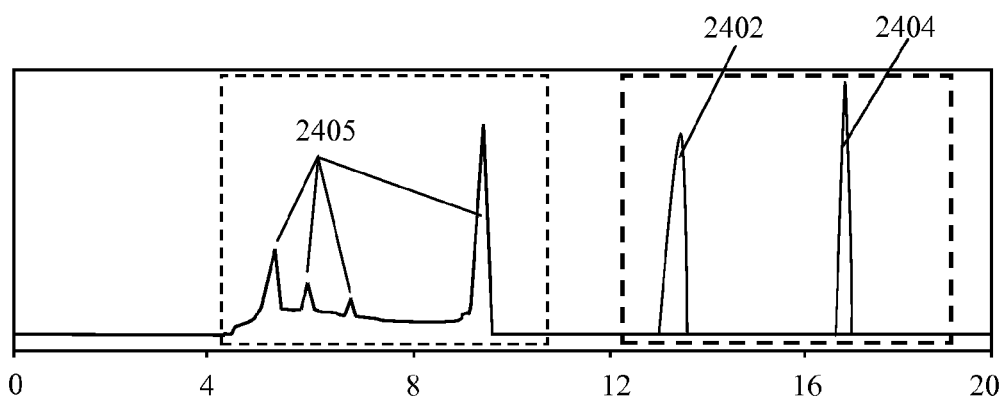

One non-limiting example of targeting nitro based explosives with a shifting reagent is to convert m-dinitro and trinitro aromatic compounds with acetone or alcohol in the presence of strong alkali into o- and p-nitro quinoid ions. FIG. 24A shows TNT 2401 and MATB 2403 being converted to quinoid ions using tetraethylammonium hydroxide and n-butanol in the presence of other components 2405 of the sample. The new quinoid ions are 2402 corresponding to 2401 and 2404 corresponding to 2403. The other components 2405 are not affected by the shifting reagent and therefore do not change. FIG. 24B shows a spectrum displaying the drift times of the sample without using a shifting reagent. The two nitro based explosives 2401 and 2403 are found in a similar drift time range as the other components 2405 which can lead to ambiguous identification of these nitro based explosives. FIG. 24C depicts the nitro based explosives 2401 and 2403 that are part of the sample being shifted to longer drift times due to shifting reagent converting them to 2402 and 2404, which have a longer drift time. FIG. 24D shows a spectrum displaying the drift times of the sample using a shifting reagent. Compounds 2402 and 2404 are at higher drift times where they are clear of interferences, such as the other components 2405.

Detecting peroxides and their precursors is very difficult for the existing ion mobility spectrometers. Current IMS based systems can detect the break down products of triacetonetriperoxide (TATP) but exhibit high false alarm rates in a short drift time detection window, and they are not able to detect hydrogen peroxide. To resolve the peroxide detection issue, several interaction mechanisms can be used to selectively adjust the drift time of components in a sample of interest, to a desired region of the IMS spectrum where few or no interfering chemicals exist. The shifting reagent may involve interacting in the gas phase with at least one component of the sample transferring protons or electrons to component molecules and forming component ions.

Peroxide based explosives include, but are not limited to: hexamethylene triperoxide diamine (HMTD), triacetonetriperoxide (TATP), organic explosive, R19, methyl ethyl ketone peroxide, acetone peroxide, peroxyacetone, TCAP, hydrogen peroxide, organic peroxides, inorganic peroxides.

A method of detecting the presence of an analyte in an ion mobility based spectrometer can comprise: supplying a shifting reagent to a sample which interacts with one or more analyte molecules in a sample; the shifting reagent has the following formulas in the next paragraphs; and resolving the analyte from other components of the sample based on their measured ion mobility characteristics.

A Peroxide targeted shifting reagent could be selected from the following molecular formulas:

Where the shifting reagent has the formula:

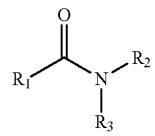

Wherein $R_1$ is alkynyl and $R_2$ and $R_3$ are independently selected from a group consisting of straight or branched chain alkyl, straight or branched chain alkenyl, straight or branched alkynyl, aryl, hereoaryl, carbocycle, heterocycle, and H. Wherein $R_2$ is alkynyl and $R_1$ and $R_3$ are independently selected from a group consisting of straight or branched chain alkyl, straight or branched chain alkenyl, straight or branched alkynyl, aryl, hereoaryl, carbocycle, heterocycle, and H. Wherein $R_3$ is alkynyl and $R_1$ and $R_2$ are independently selected from a group consisting of straight or branched chain alkyl, straight or branched chain alkenyl, straight or branched alkynyl, aryl, hereoaryl, carbocycle, heterocycle, and H. More specifically, examples of the above formula, such as, but not limited to:

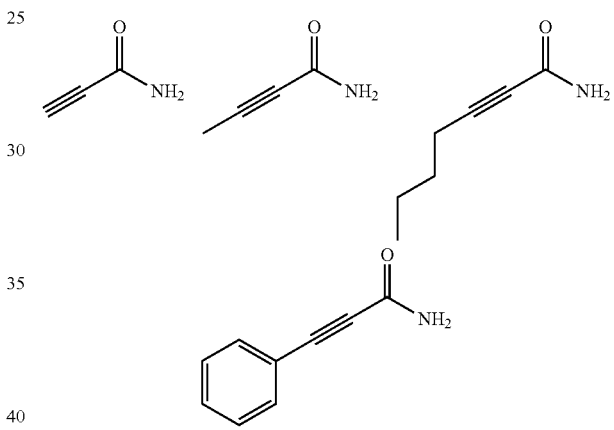

Where the shifting reagent has the formula:

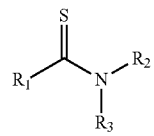

Wherein $R_1$ can be straight or branched chain alkyl, straight or branched chain alkenyl, straight or branched alkynyl, aryl, hereoaryl, carbocycle, heterocycle, and H. $R_2$ and $R_3$ are independently selected from a group consisting of straight or branched chain alkyl, straight or branched chain alkenyl, straight or branched alkynyl, aryl, hereoaryl, carbocycle, heterocycle, and H. More specifically, examples of the above formula, such as, but not limited to:

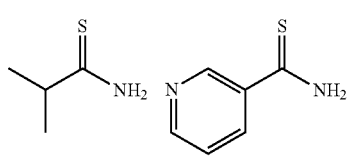

Where the shifting reagent has the formula:

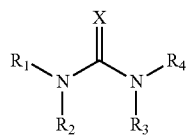

X = O, S

Wherein $R_1$ can be straight or branched chain alkyl, straight or branched chain alkenyl, straight or branched alkynyl, aryl, hereoaryl, carbocycle, heterocycle, and H. $R_2$, $R_3$, and $R_4$ are independently selected from a group consisting of straight or branched chain alkyl, straight or branched chain alkenyl, straight or branched alkynyl, aryl, hereoaryl, carbocycle, heterocycle, and H. More specifically, examples of the above formula, such as, but not limited to:

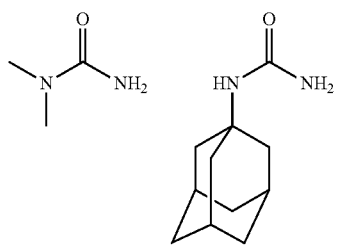

Where the shifting reagent has the formula:

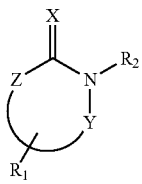

X = O, S
Y = $C_nH_{(2n-1)}$
n = 1-6
Z = C, NH, $NR_3$

Wherein $R_1$ can be straight or branched chain alkyl, straight or branched chain alkenyl, straight or branched alkynyl, aryl, hereoaryl, carbocycle, heterocycle, ketone, halogen, amino, aldehyde, alcohol, ester, ether, acid, cyano, and H. $R_2$, and $R_3$ are independently selected from a group consisting of straight or branched chain alkyl, straight or branched chain alkenyl, straight or branched alkynyl, aryl, hereoaryl, carbocycle, heterocycle, and H. More specifically, examples of the above formula, such as, but not limited to:

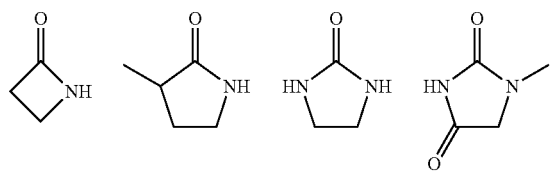

Where the shifting reagent has the formula:

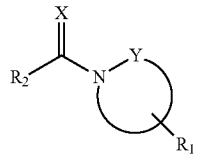

X = O, S
Y = $C_nH_{(2n-1)}$
n = 1-8

Wherein $R_1$ can be straight or branched chain alkyl, straight or branched chain alkenyl, straight or branched alkynyl, aryl, hereoaryl, carbocycle, heterocycle, ketone, halogen, amino, aldehyde, alcohol, ester, ether, acid, cyano, and H. $R_2$ is selected from a group consisting of straight or branched chain alkyl, straight or branched chain alkenyl, straight or branched alkynyl, aryl, hereoaryl, carbocycle, heterocycle, and H, $NH_2$.

Nitrate based explosives include, but are not limited to: monomethylamine nitrate (MMAN), ammonium nitrate-based explosives, Ammonit 2, Lambrit, Prillex, Cava 1a, Cava 1n, Donarit, Frangex, Gelamon 30, Gelamon 40, Gelsurite 2000, Knauerit 2, Magnafrac, Minol 2, Powermax 140, Titanite, CS Booster, Explogel, Slurmex 200, Tovex, Tutagex 110, Emex, Emulex 720, ICI-7D, Lambrex 1, Lawinit 2, magnesium nitrate, potassium nitrate, black powder nitrate.

Miscellaneous explosives include, but are not limited to: fulminates, fulminic acid, mercury(II)fulminate, potassium fulminate, silver fulminate, lead azide, nitrogen triiodide, tetrasulfur tetranitride, flash powder, black powder, smokeless powder, lead styphnate, tetrazene (tetracene), diazodinitrophenol (DDNP), detonating cords, blasting caps.

What is claimed is:

1. A ion mobility based separation method, comprising:
   a. adding a shifting reagent with one or more chiral centers to a sample, which interacts with at least one component of the sample;
   b. separating at least one component of the sample in a drift media based on their measured ion mobility characteristics; and
   c. providing energy in addition to the thermal energy at a given temperature to one or more of: the components and/or the shifting reagent and/or the drift media influencing the separation of the components in the sample.

2. The ion mobility based separation method of claim 1, wherein the energy level is tuned to alter the degree of separation of the components.

3. The ion mobility based separation method of claim 1, wherein the shifting reagent is chemoselective.

4. The ion mobility based separation method of claim 1, wherein the shifting reagent is added prior to ionization, during ionization of the sample, or after the sample has been ionized.

5. The ion mobility based separation method of claim 1, wherein the drift media comprises, one or more of noble drift gas, interactive drift gas, and/or modifier in a known ratio that is in a range of zero to one hundred percent.

6. The ion mobility based separation method of claim 5, wherein the modifier includes one or more chiral centers.

7. The ion mobility based separation method of claim 1, wherein the energy is generated using means of a range of electromagnetic energy, in particular in the visible, infrared, microwave radio range.

8. The ion mobility based separation method of claim 1, wherein the energy is from a source comprising a laser and/or radio frequency electric field.

9. The ion mobility based separation method of claim 1, further comprises using the energy to prevent neutral molecules from clustering with sample components prior to and/or during the separation in the drift media.

10. A ion mobility based spectrometer, comprising:
   a. a chiral shifting reagent added to a sample;
   b. a drift media wherein at least one component of the sample is separated based on their ion mobility characteristics; and
   c. one of more energy sources that provide energy in addition to the thermal energy at a given temperature to one or more of: the sample, and/or the shifting agent, and/or the drift media influencing the separation of the components in the sample.

11. The ion mobility based spectrometer of claim 10, wherein the energy sources can be tuned to alter the degree of interaction between: the sample components, and/or shifting reagent, and/or the drift media for the separation of the components.

12. The ion mobility based spectrometer of claim 10, wherein the shifting reagent is chemoselective.

13. The ion mobility based spectrometer of claim 10, wherein the drift media comprises; one or more of noble drift gas, interactive drift gas, and/or modifier in a known ratio that is in a range of zero to one hundred percent.

14. The ion mobility based spectrometer of claim 13, wherein the modifier has one or more chiral centers.

15. The ion mobility based spectrometer of claim 10, wherein the energy source generates a range of electromagnetic energy, in particular in the visible, infrared, microwave radio range.

16. The ion mobility based spectrometer of claim 10, wherein the energy is from a source comprising a laser and/or radio frequency electric field.

17. The ion mobility based spectrometer of claim 10, further comprises using the energy to prevent neutral molecules from clustering with sample components prior to and/or during the separation in the drift media.

* * * * *